US011320434B2

(12) United States Patent
Rose et al.

(10) Patent No.: US 11,320,434 B2
(45) Date of Patent: May 3, 2022

(54) METHOD AND APPARATUS FOR RAPID DETECTION OF SARS-COV-2

(71) Applicants: Karce Daniel Rose, Healdsburg, CA (US); Seth David Rose, Tempe, AZ (US); Neil Kempton Stone, Healdsburg, CA (US)

(72) Inventors: Karce Daniel Rose, Healdsburg, CA (US); Seth David Rose, Tempe, AZ (US); Neil Kempton Stone, Healdsburg, CA (US)

(73) Assignees: Karce Daniel Rose, Healdsburg, CA (US); David Seth Rose, Tempe, AZ (US); Neil Kempton Stone, Healdsburg, CA (US)

( * ) Notice: Subject to any disclaimer, the term of this patent is extended or adjusted under 35 U.S.C. 154(b) by 0 days.

(21) Appl. No.: 17/338,640

(22) Filed: Jun. 3, 2021

(65) Prior Publication Data

US 2021/0405051 A1 Dec. 30, 2021

Related U.S. Application Data

(60) Provisional application No. 63/034,482, filed on Jun. 4, 2020.

(51) Int. Cl.
*G01N 33/53* (2006.01)
*G01N 21/64* (2006.01)
*G01N 33/569* (2006.01)

(52) U.S. Cl.
CPC ... *G01N 33/56983* (2013.01); *G01N 21/6428* (2013.01); *G01N 2021/6439* (2013.01); *G01N 2333/165* (2013.01)

(58) Field of Classification Search
None
See application file for complete search history.

(56) References Cited

U.S. PATENT DOCUMENTS 11,129,890 B1 * 9/2021 Sun .................. A61K 39/12

OTHER PUBLICATIONS

Pereira et al., PLoS ONE, 2011, 6(2):317016, 10 pages. (Year: 2011).*
Adams et al., J. Am. Chem. Soc., 2002, 124:6063-6076. (Year: 2002).*
Juskowiak II, G. L., Ph.D. Dissertation, University of California, Irvine, 2009. "Sequence-Specific Reactivity of Short Peptides: Peptide Photooxidative Fluorogenesis and Peptide Tags for Small Molecule Fluorescent Probes." Chapter 2, "Peptide Tags used for Labeling Proteins in Living Cells with Small Molecule Fluorescent Probes" and Chapter 6, "Short Peptide Tags for Small Molecule Fluorogenic Probes."
Scheck, R. A. and Schepartz, A., "Surveying Protein Structure and Function Using Bis-Arsenical Small Molecules," Acc Chem Res., 44(9):654-665 (2011).
Wang, T., et al., "Prospecting the Proteome: Identification of Naturally Occurring Binding Motifs for Biarsenical Probes," ChemBioChem, 8:1937-1940 (2007).

* cited by examiner

*Primary Examiner* — Stacy B Chen
(74) *Attorney, Agent, or Firm* — Nixon & Vanderhye P.C.

(57) ABSTRACT

A method and apparatus for comfortably, rapidly, and inexpensively collecting a sample from one or more test subjects and analyzing it, singly or pooled with other samples, for presence of SARS-CoV-2. Saliva, nasal drainage, or other body fluids may be collected from one or more test subjects and examined by means of fluorimetry. Mass rapid screening for SARS-CoV-2 is a valuable public health tool to reduce the transmission of COVID-19 while permitting business activity to resume.

21 Claims, 19 Drawing Sheets

Specification includes a Sequence Listing.

METHOD AND APPARATUS FOR RAPID DETECTION OF SARS-COV-2

RELATED APPLICATIONS

This application claims the benefit of U.S. Ser. No. 63/034,482 filed Jun. 4, 2020, which is incorporated herein by reference in its entirety.

FIELD OF THE INVENTION

Embodiments disclosed herein relate generally to systems, devices, compositions of matter, and methods for testing for the presence of Severe Acute Respiratory Syndrome Coronavirus 2 (SARS-CoV-2) in bodily fluid or other samples. More specifically, certain embodiments concern systems, devices, compositions of matter, and methods that can be implemented to collect a saliva or nasal drainage sample from one or more test subjects and rapidly, comfortably, and inexpensively examine it for presence of Severe Acute Respiratory Syndrome Coronavirus 2 (SARS-CoV-2) by means of probing with electromagnetic waves.

INCORPORATION OF SEQUENCE LISTING

The contents of the text file named "DR20210603_501001US_Sequence_Listing_ST25.txt", which was created on Aug. 16, 2021, and is 4.0 KB in size, are hereby incorporated by reference in their entirety.

BACKGROUND OF THE INVENTION

The recent pandemic of COVID-19 infection to millions of people worldwide presents an urgent need for a diagnosis method capable of quickly, efficiently, and reliably detecting the related virus (e.g., SARS-CoV-2) in biological samples.

SUMMARY OF THE INVENTION

The systems, devices, and methods disclosed herein each have several aspects, no single one of which is solely responsible for their desirable attributes. Without limiting the scope of the claims, some prominent features will now be discussed briefly. Numerous other embodiments are also contemplated, including embodiments that have fewer, additional, and/or different components, steps, features, objects, benefits, and advantages. The components, aspects, and steps may also be arranged and ordered differently. Exemplary devices of the present invention may comprise a salivation stimulating scent sticker, a sample collector, a filter, a fluorescent dye (fluorophore) that changes optical properties upon protein binding, or alternatively a pre-fluorescent substance (i.e., a nonfluorescent substance that becomes fluorescent upon combination with the protein), and an analyzer, which may be combined into a single device. An advantage of pre-fluorescent substances is that they do not produce significant background fluorescence in the unbound state, thereby enhancing detectability when protein bound. After considering this discussion, and particularly after reading the section entitled "Brief Description of the Drawings," one will understand how the features of the devices and methods disclosed herein can provide advantages over other known devices and methods.

In one aspect, the instant disclosure provides herein a method of detecting SARS-CoV-2 in a biological sample. In some embodiments, the method comprises:
i) providing a composition for detection, comprising the biological sample and a fluorophore, wherein the fluorophore is capable of binding chemically with SARS-CoV-2;
ii) providing to the composition for detection a light comprising a first wavelength range (maximal wavelength at $\lambda_1$) capable of energizing the fluorophore after binding chemically with SARS-CoV-2; and
iii) measuring fluorescence emitted by the fluorophore at a second wavelength range (maximal wavelength at $\lambda_2$),
wherein SARS-CoV-2 is detected in the biological sample if the level of the detected fluorescence in iii) is higher than a control sample fluorescence level.

In some embodiments, the method comprises:
i) providing a composition for detection, comprising the biological sample and a first fluorophore, wherein the first fluorophore is capable of binding chemically with SARS-CoV-2;
ii) providing to the composition for detection a light comprising a first wavelength range (maximal wavelength at $\lambda_1$) capable of energizing the first fluorophore after binding chemically with SARS-CoV-2;
iii) providing to the composition a second fluorophore that is energized directly or indirectly by the first fluorophore which has been energized; and
iv) measuring fluorescence emitted by the second fluorophore at a third wavelength range (maximal wavelength at $\lambda_3$),
wherein SARS-CoV-2 is detected in the biological sample if the level of the detected fluorescence in iv) is higher than a control sample fluorescence level.

In some embodiments, the fluorophore or the first fluorophore comprises a biarsenical dye. In some embodiments, the biarsenical dye comprises the structure of Formula I:

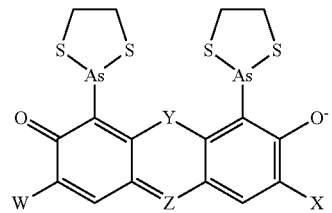

Formula I wherein,
W is a hydrogen (H) or bromine (Br);
X is a hydrogen (H) or bromine (Br);
Y is an oxygen (O) or sulfur (S); and
Z is a nitrogen (N) or C—$C_6H_4COOH$,
or a chemically acceptable salt or precursor thereof. In some embodiments, the biarsenical dye comprises ReAsH-$EDT_2$, ReAsHO, HoXAsH-$EDT_2$, CHoXAsH-$EDT_2$, FlAsH-$EDT_2$, 5/6-CrAsH-$EDT_2$, AF568-FlAsH, Biotin-FlAsH (Bio-FlAsH), β-alanyl FlAsH, AsCy3, CrAsH-$EDT_2$, sFlAsH-$EDT_2$, F2-FlAsH-$EDT_2$, SpLAsH-$EDT_2$-Alexa594, CaG FlAsH-$EDT_2$, or AsCy3-$EDT_2$, such as one of below structures:

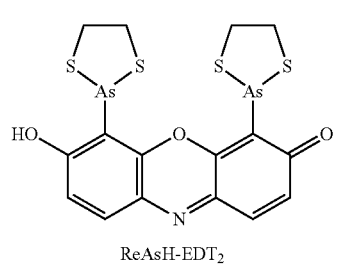
ReAsH-EDT₂
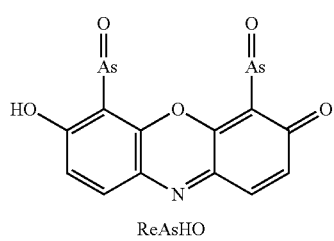
ReAsHO
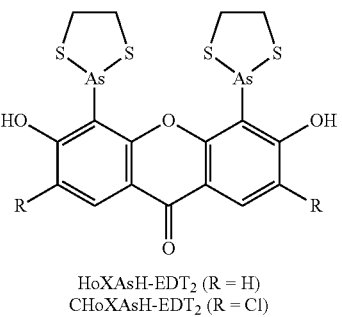
HoXAsH-EDT₂ (R = H)
CHoXAsH-EDT₂ (R = Cl)
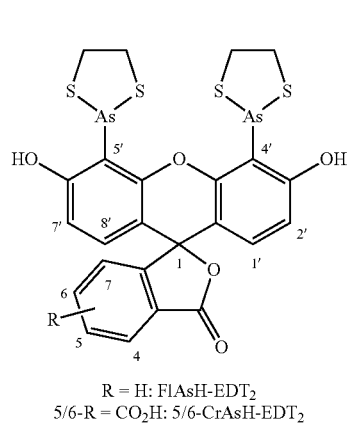
R = H: FlAsH-EDT₂
5/6-R = CO₂H: 5/6-CrAsH-EDT₂
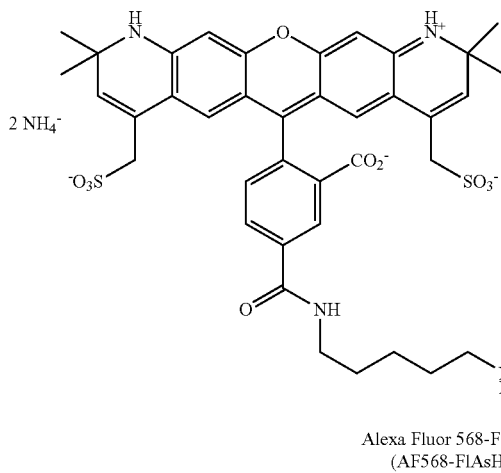
Alexa Fluor 568-FlAsH
(AF568-FlAsH)
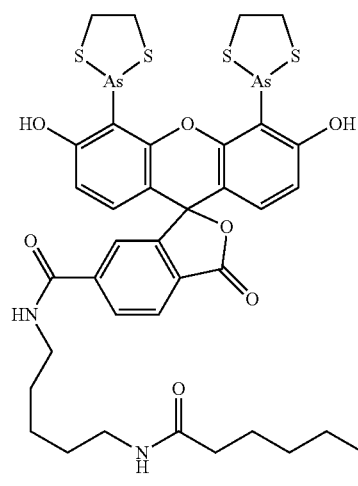
Biotin-FlAsH (Bio-FlAsH)
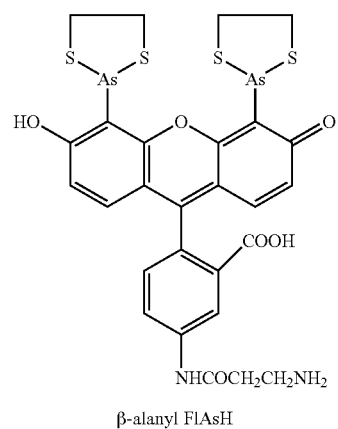
β-alanyl FlAsH -continued
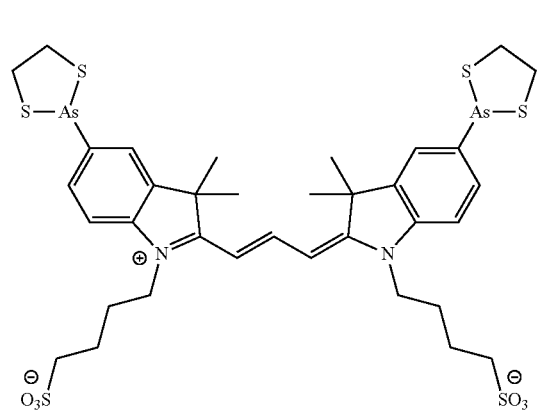
AsCy3
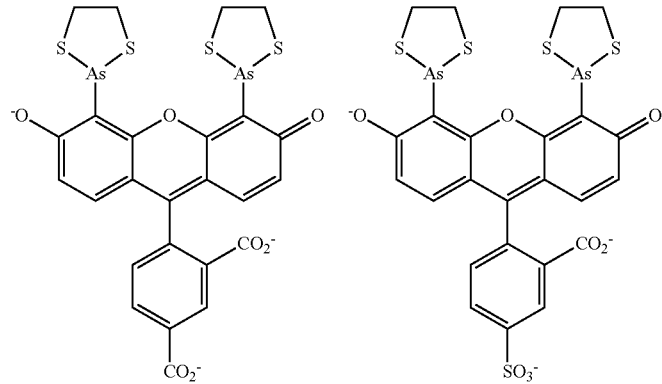
CrAsH-EDT$_2$    sFlAsH-EDT$_2$
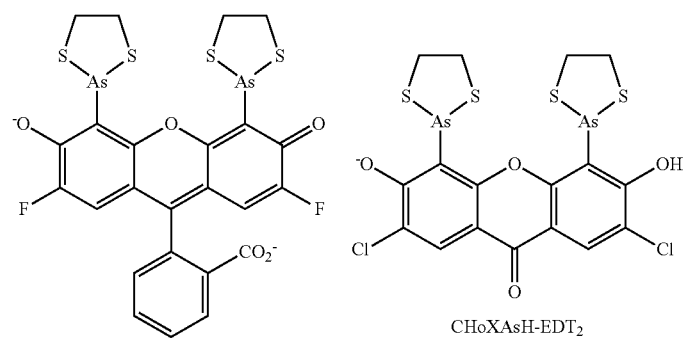
F2-FlAsH-EDT$_2$    CHoXAsH-EDT$_2$
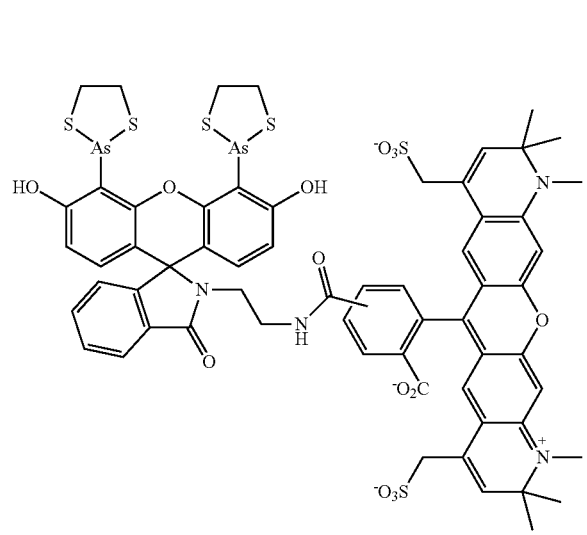
SpLAsH-EDT-Alexa594
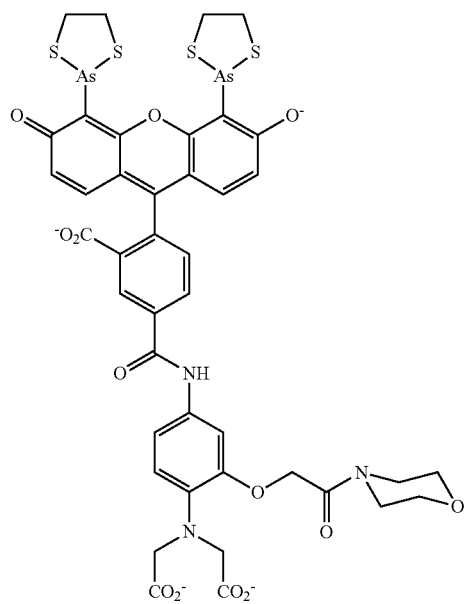
CaG FlAsH-EDT$_2$ AsCy3-EDT₂

In some embodiments, the biarsenical dye comprises the structure of Formula II or III:

Formula II (FlAsH-EDT₂)

Formula III (ReAsH-EDT₂)

or a chemically acceptable salt or precursor thereof. The term "FlAsH" refers to 2-(4,5-di(1,3,2-dithiarsolan-2-yl)-6-hydroxy-3-oxo-3H-xanthen-9-yl)benzoic acid.

In some embodiments, the fluorophore or the first fluorophore described herein is energized or excited by a light comprising a first wavelength range of, e.g., about 360 nm to about 652 nm, with a maximal wavelength at $\lambda_1$. In some embodiments, $\lambda_1$ is at a wavelength of about 360 nm to about 652 nm. In some embodiments, $\lambda_1$ is about 508 nm or about 593 nm.

In some embodiments, only one fluorophore is used to chemically bind with a target (e.g., the K9K peptide described herein). Under these situations, the energized fluorophore is capable of emitting fluorescence at a second wavelength range (maximal wavelength at $\lambda_2$). In some embodiments, $\lambda_2$ is about 528 nm or about 608 nm.

In some embodiments, at least two fluorophores are used to combine with a target (e.g., the K9K peptide described herein) for detection of virus. In some embodiments, a first fluorophore is capable of chemically binding with the target (e.g., the K9K peptide described herein). Under these situations, the energized first fluorophore is capable of transferring all or at least a part of its energy to energize a second fluorophore and promote the energized second fluorophore to emit fluorescence at a third wavelength range (maximal wavelength at $\lambda_3$). In some embodiments, $\lambda_3$ is at a wavelength within a range of about 350 nm to about 790 nm. In some embodiments, the first fluorophore, after transferring a part of its energy to and thus energizing the second fluorophore, still emits fluorescence in a certain wavelength range. In some embodiments, the first fluorophore, after transferring all its energy to and thus energizing the second fluorophore, does not emit any fluorescence.

In some embodiments, the fluorophore or the first fluorophore is capable of binding chemically with a tetracysteine sequence of a SARS-CoV-2 protein and/or cysteine pairs in adjacent proteins. In some embodiments, the fluorophore or the first fluorophore is capable of binding chemically with a tetracysteine sequence of a SARS-CoV-2 spike protein and/or cysteine pairs in adjacent spike proteins. In some embodiments, the tetracysteine sequence comprises a $C_1C_2X_nC_3C_4$ (SEQ ID NO: 1), wherein $C_1$-$C_4$ refer to four cysteine residues, $X_n$ refers to any number (n) of amino acid residue(s), and n is an integer selected from 1 to 29. In some embodiments, n is from 1, 2, 3, 4, 5, 6, 7, 8, 9, 10, 11, 12, 13, 14, 15, 16, 17, 18, 19, 20, or more. In some embodiments, n is 1. In some embodiments, n is 2. In some embodiments, n is 4. For example, when a fluorophore binds to a tetracysteine sequence on a single SARS-CoV-2 spike protein strand, n may be 3, 4, 5, 10, 11, or 16. When a fluorophore binds to two cysteine pairs localized on different spike protein strands, n does not apply. In some embodiments, the tetracysteine sequence described herein comprises CCSCGSCC (SEQ ID NO: 2).

In some embodiments, the biological sample described herein is derived from saliva, oral fluid, nasal drainage fluid, nasal swab residue, nasopharyngeal swab residue, pharyngeal swab residue, upper and/or lower respiratory tract aspirate, or stool of one or more subjects. In some embodiments, the biological sample comprises a body fluid of one or more subjects.

In some embodiments, the biological sample described herein is filtered to remove any debris, cells, and/or tissues, prior to addition of the fluorophore or the first fluorophore. In some embodiments, the filtering is performed with i) a filter made up of polyethersulfone (PES), polyvinylidene fluoride (PVDF), or any suitable material that does not inhibit the passage of virus, or other materials; and/or ii) a filter comprising a plurality of pores of about 0.05 to about 0.5 micron pore size, preferably 0.22 micron pore size.

In some embodiments, the composition for detection described herein further comprises a reducing agent. Exemplary reducing agents may include tris(2-carboxyethyl)phosphine (TCEP), British anti-Lewisite (BAL, a.k.a., dimercaprol), 2-aminoethanethiol (cysteamine), cysteine, dithiobutylamine (DTBA), dithioerythritol (DTE), dithiothreitol (DTT), glutathione, β-mercaptoethanol (β-ME), sodium 2-mercaptoethanesulfonate (MESNa), or their chemically acceptable salts.

In some embodiments, the method described herein further comprises heating the composition for detection to at least a temperature $T_1$, prior to the measuring in step iii) or iv). In some embodiments, the temperature $T_1$ may be at least about 15° C., 20° C., 25° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or higher. In some embodiments, the temperature $T_1$ may be at least about 40° C. In some embodiments, the heating is provided by a heating element.

In some embodiments, the light in step ii) passes through the composition for detection a plurality of times to enhance light absorption while measuring in step iii) or iv). In some embodiments, the light in step ii) passes through the composition for detection a plurality of times by reflection from a mirror and/or other reflecting surfaces. Such reflection may help maximizing detection of fluorescence.

In some embodiments, the method described herein further comprises spinning the biological sample in a centrifuge to concentrate any SARS-CoV-2 in the biological sample, prior to addition of the fluorophore or the first fluorophore. Such centrifugation may be able to increase sensitivity of detection of emitted fluorescence.

In some embodiments, the method described herein further comprises adhering any SARS-CoV-2 in the biological sample with a viral selective surface or membrane, prior to addition of the fluorophore or the first fluorophore, or by application of the biological sample to an adhered fluorophore (e.g., adhered FlAsH). In some embodiments, the method described herein further comprises adhering any SARS-CoV-2 in the biological sample directly to an immobilized fluorophore (e.g., FlAsH). Such adhering may be able to increase sensitivity of detection of fluorescence and/or specificity for SARS-CoV-2. In some embodiments, the viral selective surface or membrane or the adhered fluorophore is capable of adhering to the SARS-CoV-2 spike protein.

In another aspect, the instant disclosure provides herein a composition comprising a biological sample comprising SARS-CoV-2 and a fluorophore, wherein the fluorophore is capable of binding chemically with SARS-CoV-2, and wherein the fluorophore, when bound to SARS-CoV-2, is capable of: 1) being energized by a light comprising a first wavelength range (maximal wavelength at $\lambda_1$); and 2) emitting fluorescence at a second wavelength range (maximal wavelength at $\lambda_2$).

In another aspect, the instant disclosure provides herein a composition comprising a biological sample comprising SARS-CoV-2, a first fluorophore, and a second fluorophore, wherein the first fluorophore is capable of binding chemically with SARS-CoV-2 and being energized by a light comprising a first wavelength range (maximal wavelength at $\lambda_1$), and wherein the second fluorophore is capable of being energized directly or indirectly by the energized first fluorophore and emitting fluorescence at a third wavelength range (maximal wavelength at $\lambda_3$).

In some embodiments, the fluorophore or the first fluorophore described herein comprises a biarsenical dye. In some embodiments, the biarsenical dye comprises the structure of Formula I:

Formula I wherein,
W is a hydrogen (H) or bromine (Br);
X is a hydrogen (H) or bromine (Br);
Y is an oxygen (O) or sulfur (S); and
Z is a nitrogen (N) or C—$C_6H_4$COOH, or a chemically acceptable salt or precursor thereof. In some embodiments, the biarsenical dye comprises ReAsH-EDT$_2$, ReAsHO, HoXAsH-EDT$_2$, CHoXAsH-EDT$_2$, FlAsH-EDT$_2$, 5/6-CrAsH-EDT$_2$, AF568-FlAsH, Biotin-FlAsH (Bio-FlAsH), β-alanyl FlAsH, AsCy3, CrAsH-EDT$_2$, sFlAsH-EDT$_2$, F2-FlAsH-EDT$_2$, SpLAsH-EDT$_2$-Alexa594, CaG FlAsH-EDT$_2$, or AsCy3-EDT$_2$, such as one of structures described herein in the instant application. In some embodiments, the biarsenical dye comprises the structure of Formula II or III:

Formula II (FlAsH-EDT$_2$)

Formula III (ReAsH-EDT$_2$)

or a chemically acceptable salt or precursor thereof.

In some embodiments, the fluorophore or the first fluorophore in the composition described herein is energized or excited by a light comprising a first wavelength range of, e.g., about 360 nm to about 652 nm, with a maximal wavelength at $\lambda_1$. In some embodiments, $\lambda_1$ is at a wavelength of about 360 nm to about 652 nm. In some embodiments, $\lambda_1$ is about 508 nm or about 593 nm.

In some embodiments, only one fluorophore is used to chemically bind with a target (e.g., the K9K peptide described herein). Under these situations, the energized fluorophore is capable of emitting fluorescence at a second wavelength range (maximal wavelength at $\lambda_2$). In some embodiments, $\lambda_2$ is about 528 nm or about 608 nm.

In some embodiments, at least two fluorophores are used to combine with a target (e.g., the K9K peptide described herein). In some embodiments, a first fluorophore is capable of chemically binding with the target (e.g., the K9K peptide described herein). Under these situations, the energized first fluorophore is capable of energizing a second fluorophore and promoting the energized second fluorophore to emit fluorescence at a third wavelength range (maximal wavelength at $\lambda_3$). In some embodiments, $\lambda_3$ is at a wavelength within a range of about 350 nm to about 790 nm. In some embodiments, the energized first fluorophore, after transferring a part of its energy to and thus energizing the second fluorophore, still emits fluorescence in a certain wavelength range. In some embodiments, the energized first fluorophore, after transferring all its energy to and thus energizing the second fluorophore, does not emit any fluorescence.

In some embodiments, the fluorophore or the first fluorophore in the composition described herein is capable of binding chemically with a tetracysteine sequence of a SARS-CoV-2 protein and/or cysteine pairs in adjacent proteins. In some embodiments, the fluorophore or the first fluorophore is capable of binding chemically with a tetracysteine sequence of a SARS-CoV-2 spike protein and/or cysteine pairs in adjacent spike proteins. In some embodiments, the tetracysteine sequence comprises a $C_1C_2X_nC_3C_4$ (SEQ ID NO: 1), wherein $C_1$-$C_4$ refer to four cysteine residues, $X_n$ refers to any number (n) of amino acid residue(s), and n is an integer selected from 1 to 29. In some embodiments, n is from 1, 2, 3, 4, 5, 6, 7, 8, 9, 10, 11, 12, 13, 14, 15, 16, 17, 18, 19, 20, or more. In some embodiments, n is 1. In some embodiments, n is 2. In some embodiments, n is 4. For example, when a fluorophore binds to a tetracysteine sequence on a single SARS-CoV-2 spike protein strand, n may be 3, 4, 5, 10, 11, or 16. When a fluorophore binds to two cysteine pairs localized on different spike protein strands, n does not apply. In some embodiments, the tetracysteine sequence described herein comprises CCSCGSCC (SEQ ID NO: 2). In some embodiments, the tetracysteine sequence described herein comprises $C_1C_2SC_5GSC_3C_4$ (SEQ ID NO: 2), and one arsenic of the fluorophore may bind to $C_2$ and $C_5$ while the other arsenic of the fluorophore binds to $C_3$ and $C_4$.

In some embodiments, the biological sample in the composition described herein is derived from saliva, oral fluid, nasal drainage fluid, nasal swab residue, nasopharyngeal swab residue, pharyngeal swab residue, upper and/or lower respiratory tract aspirate, or stool of one or more subjects. In some embodiments, the biological sample comprises a body fluid of one or more subjects.

In some embodiments, the biological sample in the composition described herein is filtered to remove any debris, cells, and/or tissues, prior to addition of the fluorophore or the first fluorophore. In some embodiments, the filtering is performed with i) a filter made up of polyethersulfone (PES), polyvinylidene fluoride (PVDF), or any suitable material that does not inhibit the passage of virus, or other materials; and/or ii) a filter comprising a plurality of pores of about 0.05 to about 0.5 micron pore size, preferably 0.22 micron pore size.

In some embodiments, the composition described herein further comprises a reducing agent. Exemplary reducing agent may include tris(2-carboxyethyl)phosphine (TCEP), British anti-Lewisite (BAL, a.k.a., dimercaprol), 2-aminoethanethiol (cysteamine), cysteine, dithiobutylamine (DTBA), dithioerythritol (DTE), dithiothreitol (DTT), glutathione, (3-mercaptoethanol (β-ME), sodium 2-mercaptoethanesulfonate (MESNa), or their chemically acceptable salts.

In some embodiments, the composition described herein is heated to at least a temperature $T_1$. In some embodiments, the temperature $T_1$ may be at least about 15° C., 20° C., 25° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or higher. In some embodiments, the temperature $T_1$ may be at least about 40° C. In some embodiments, the heating is provided by a heating element.

In some embodiments, any SARS-CoV-2 in the biological sample in the composition described herein is concentrated by i) spinning the biological sample in a centrifuge; and/or ii) adhering SARS-CoV-2 in the biological sample with a viral selective surface or membrane, prior to addition of the fluorophore or the first fluorophore; and/or iii) adhering SARS-CoV-2 in the biological sample to an adhered fluorophore (e.g., adhered FlAsH). Such spinning or centrifugation may be able to increase sensitivity of detection of emitted fluorescence. Such adhering may be able to increase sensitivity of detection of fluorescence and/or specificity for SARS-CoV-2.

In some embodiments, any SARS-CoV-2 in the biological sample in the composition described herein is adhered to a viral selective surface or membrane. In some embodiments, the viral selective surface or membrane is capable of adhering to the SARS-CoV-2 spike protein.

In some embodiments, the composition described herein further comprises an adhered fluorophore (e.g., FlAsH). In some embodiments, the adhered fluorophore is capable of adhering to the SARS-CoV-2 spike protein.

In some embodiments, the composition described herein is used for detection of the existence of SARS-CoV-2 in the biological sample by detection of fluorescence emitted by the fluorophore or the second fluorophore, when the fluorophore or the first fluorophore bound to SARS-CoV-2.

In another aspect, the instant disclosure provides a kit for detection of the existence of SARS-CoV-2 in a biological sample, comprising:

i) a composition described herein; and ii) optionally, a manual of instructions.

In some embodiments, the kit described herein further comprises a filter to remove debris, cells, and/or tissues in the biological sample. In some embodiments, the filter i) is made up of polyethersulfone (PES), polyvinylidene fluoride (PVDF), or any suitable material that does not inhibit the passage of virus, or other materials; and/or ii) comprises a plurality of pores of about 0.05 to about 0.5 micron pore size, preferably 0.22 micron pore size.

In some embodiments, the kit described herein further comprises a device to stimulate production of the biological sample by one or more subjects. In some embodiments, the device to stimulate production of the biological sample by the one or more subjects comprises a scented sticker to stimulate saliva production.

In some embodiments, the kit further comprises a viral selective surface or membrane, or an adhered fluorophore, capable of adhering any SARS-CoV-2 in the biological sample, as described herein. In some embodiments, the viral selective surface or membrane or the adhered fluorophore is capable of adhering to the SARS-CoV-2 spike protein.

In another aspect, the instant disclosure provides a system for detection of the existence of SARS-CoV-2 in a biological sample, comprising:

i) a first device capable of collecting or containing a biological sample;

ii) a second device containing a composition described herein;

iii) an emitter capable of emitting light comprising the first wavelength range (maximal wavelength at $\lambda_1$) through the composition in ii) when mixed with the biological sample; and iv) a detector capable of measuring fluorescence emitted by the fluorophore described herein at the second wavelength range (maximal wavelength at $\lambda_2$) or the second fluorophore described herein at the third wavelength range (maximal wavelength at $\lambda_3$).

In some embodiments, the system described herein further comprises a filter to remove debris, cells, and/or tissues in the biological sample. In some embodiments, the filter i) is made up of polyethersulfone (PES), polyvinylidene fluoride (PVDF), or any suitable material that does not inhibit the passage of virus, or other materials; and/or ii) comprises a plurality of pores of about 0.05 to about 0.5 micron pore size, preferably 0.22 micron pore size.

In some embodiments, the system described herein further comprises a device to heat the composition.

In some embodiments, the system described herein further comprises a device to stimulate production of the biological sample by one or more subjects. In some embodiments, the device to stimulate production of the biological sample by the one or more subjects comprises a scented sticker to stimulate saliva production.

In some embodiments, the system described herein further comprises an optical device to reflect the light a plurality of times through the composition. In some embodiments, the optical device comprises a mirror and/or other reflecting surfaces.

In some embodiments, the system described herein further comprises a centrifuge to concentrate any SARS-CoV-2 in the biological sample. Such centrifugation may be able to increase sensitivity of detection of emitted fluorescence.

In some embodiments, the system described herein further comprises a viral selective surface or membrane capable or an adhered fluorophore of adhering any SARS-CoV-2 in the biological sample. Such adhering may be able to increase sensitivity of detection of fluorescence and/or specificity for SARS-CoV-2. In some embodiments, the viral selective surface or membrane or the adhered fluorophore is capable of adhering to the SARS-CoV-2 spike protein. Some embodiments relate to methods, systems and kits for detecting (e.g., SARS-CoV-2) utilizing a device or apparatus as described herein with any of the methods set forth herein, including the methods described in the Summary of the Invention, the detailed description and the claims as filed.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

DETAILED DESCRIPTION

Figure 1:
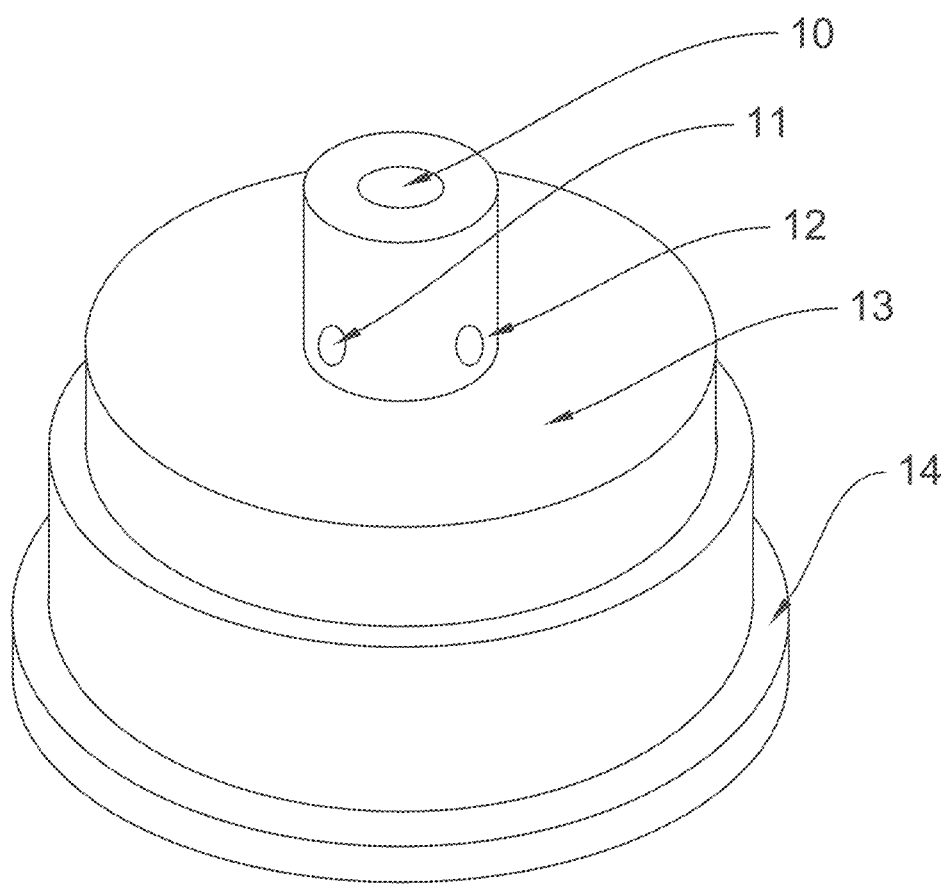
FIG. 1 is a graph schematically illustrating a three-dimensional isometric view of a non-limiting example of an analyzer 13, which is constructed of opaque material that prevents entry of external light. It will be seen that the analyzer comprises a portal 10 for partially inserting a test tube containing a filtered saliva sample, to which a fluorophore has been added. Said fluorophore when combined chemically with SARS-CoV-2 proteins becomes fluorescent at a wavelength that can be detected. Light waves are generated by the emitter 11 thereby penetrating said test tube and sample material. Fluorescence, if any, is received by the photodetector 12. The base of the analyzer 13 is designed with an offset 14 or offsets to prevent entry of light that would adversely affect the accuracy of the test.
Figure 2:
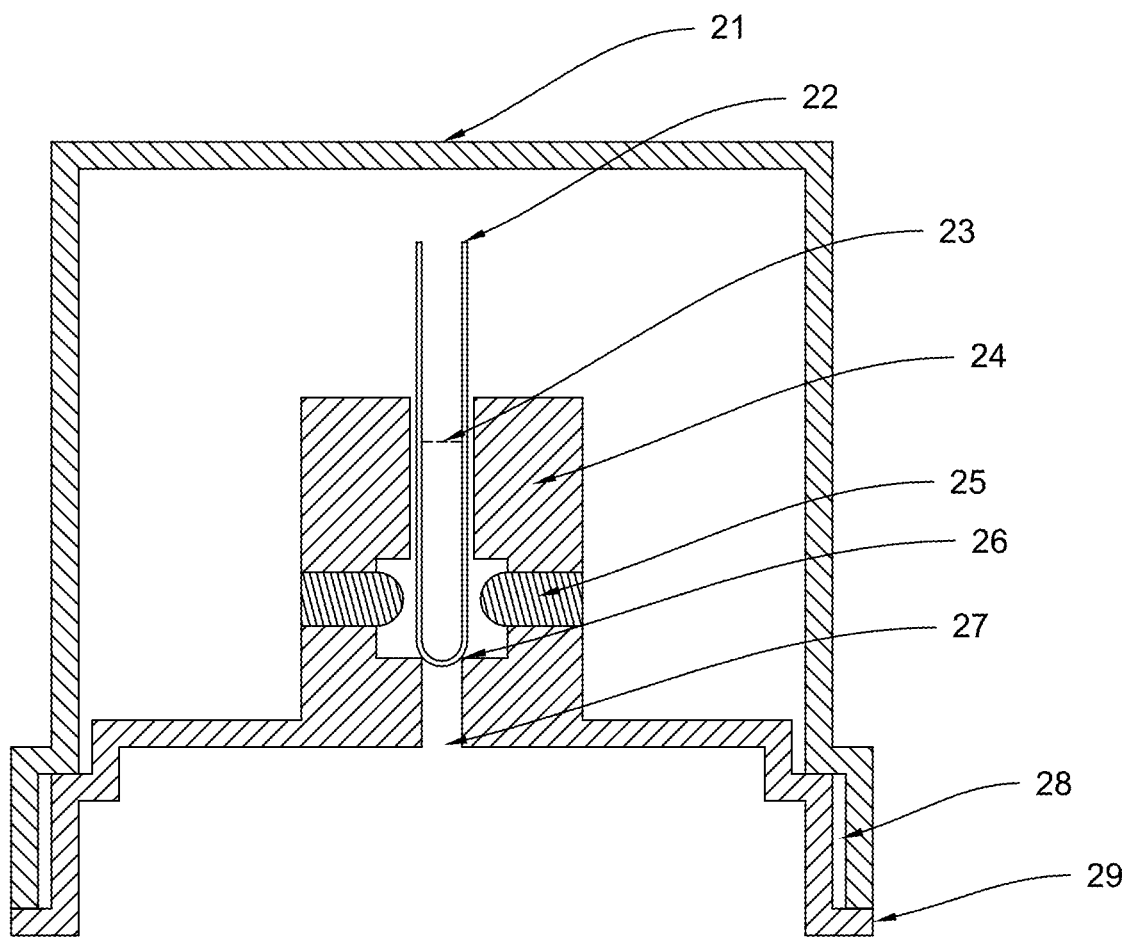
FIG. 2 is a graph schematically illustrating a cross sectional side view of a non-limiting example of an analyzer 29, test tube 22, and cover 21. A filtered saliva sample and fluorophore (23) have been added to the test tube 22 and agitated to promote complete mixing and chemical reaction of the two materials. Said tube is supported by the edges of a hole 26 in the base 29 and maintained vertically by a projection 24 that also serves as a housing for photodetectors 25 and emitters (not seen in cross section). Said hole 26 serves both as support of said tube 22 and as a means of drainage of any fluid or debris that might enter. Said accumulated fluid exits the base 29 via a drainage port 27. An effective light trap 28 is created by offsets in the cover 21 and the base 29. A photodetector 25 is positioned in close proximity to the test tube 22 and saliva/fluorophore material 23 to enhance detection of any fluorescence. An emitter is positioned at right angles to the photodetector 25 and is not seen in this cross section.
Figure 3:
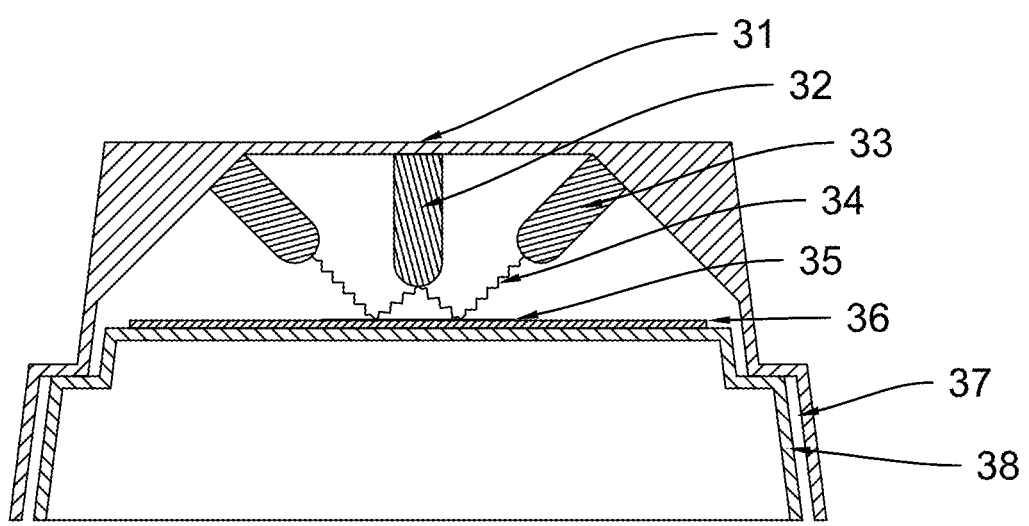
FIG. 3 is a graph schematically illustrating a cross sectional side view of a non-limiting example of an analyzer 31, slide 36, and base 38. An LED emitter 32 is positioned in close proximity to a slide 36 containing a mixture 35 of a filtered saliva sample and a fluorophore. Said slide may have been coated with a material that enhances adhesion of viruses, enabling excess saliva to be irrigated away, thereby concentrating virus material to enhance detection. Said slide may also comprise a membrane or other material that enhances viral adhesion. An emitter 32 irradiates the sample from an angle, typically 90 degrees, to minimize the amount of emitted light 34 striking the photodetector 33. One or more photodetectors (33) are positioned in close proximity to the sample material 35 to receive fluorescence from SARS-CoV-2 that has combined chemically with the fluorophore. Said photodetectors may be positioned vertically or at an angle to minimize unwanted light. If fluorescence is detected, the analyzer indicates a result that COVID-19 has been detected. The test one or more subjects who have provided the saliva sample are informed of the result, as are any relevant public health authorities.

The instant disclosure is related to, among other things, methods of detecting COVID-19-related virus (e.g., SARS-CoV-2) in a biological sample. In non-limiting embodiments, the methods utilize at least one fluorophore capable of chemically binding with a viral peptide (e.g., spike proteins on SARS-CoV-2) and emitting fluorescence when energized by a light comprising an excitation wavelength for the at least one fluorophore. When mixed with a biological sample, the at least one fluorophore may chemically bind with a viral peptide (e.g., spike proteins on SARS-CoV-2) or any COVID-19-related virus (e.g., SARS-CoV-2) which may exist in the biological sample and, upon being energized by an excitation light, emit fluorescence in a certain wavelength range, which may be detected and identified as a marker of existence of COVID-19-related virus (e.g., SARS-CoV-2) in the biological sample. The instant disclosure further provides compositions of such fluorophore-virus mixture for diagnosis, kits comprising such compositions, and systems comprising devices for collecting, mixing, and/or detecting the virus in the biological sample. In non-limiting embodiments, the methods, compositions, kits, and systems described herein provide a quick, efficient, and cost-effective detection method for COVID-19-related virus (e.g., SARS-CoV-2) in the biological sample.

In the following detailed description, reference is made to the accompanying drawings, which form a part hereof. The illustrative embodiments described in the detailed description, drawings, and claims are not meant to be limiting. Other embodiments may be utilized, and other changes may be made, without departing from the spirit or scope of the one or more subjects matter presented herein. It will be readily understood that the aspects of the present disclosure, as generally described herein, and illustrated in the Figures, can be arranged, substituted, combined, and designed in a wide variety of different configurations, all of which are explicitly contemplated and made part of this disclosure.

COVID-19 and SARS-CoV-2 Virus

Some microorganisms produce communicable diseases in humans, affecting many persons at the same time (outbreaks) in a region or community (epidemic), or prevalent over a whole country, continent, or the world (pandemic). Examples of pandemics causing extensive injury and loss of life include Coronavirus disease 19 (COVID-19), influenza, HIV, cholera, bubonic plague, smallpox, and tuberculosis. Public health measures to reduce the spread of communicable diseases include public education, screening, isolation, contact tracing, travel restriction, and limitation of gathering in groups. Screening may include administration of a questionnaire, checking body temperature, observing physical characteristics, and testing physiologic samples from persons. A nasal swab obtained from a person with a coronavirus infection contains an average of 10,000,000 viral copies per sample, ten times as many as found with influenza. Saliva contains between 10,000 (ten thousand) and 10,000,000,000 (ten billion) viral copies per milliliter early in the course of infection. The spike protein of SARS-CoV-2 that imparts the crown-like appearance to the virus includes a cysteine-rich region that will have an affinity for certain fluorescent dyes or pre-fluorescent substances i.e., substances that become fluorescent upon chemical combination with the protein).

Saliva collection devices are taught in U.S. Pat. No. 9,498,191 B2, US 2012/0046574 A1, U.S. Pat. No. 8,273, 305 B2, and others. A1. A ligand immobilized on a disposable adsorptive membrane enhances the collection of viral particles, is taught in US 2018/0094247 A1 and U.S. Pat. No. 8,846,203 B2. A scented sticker is taught in U.S. Pat. No. 4,283,011, and a scented sticker that attaches to a container is taught in U.S. Pat. No. 10,328,172 B2. An LED-based colorimeter is taught in WO 2017/029681. Spectrometers that can be comfortably held by a user with one or two hands while operating the device, are taught in U.S. Pat. No. 7,791,027 B2, U.S. Pat. No. 7,236,243 B2, US 2019/0033130 A1, and U.S. Pat. No. 7,505,128 B2, among others. A spectrometer with provision for a container system is taught in U.S. Pat. No. 7,542,138 B2. Specifically, a handheld spectrometer that provides a method for rapid and cost-effective screening of various protein-based compounds such as bacteria, virus, drugs, and tissue abnormalities is taught in U.S. Pat. No. 10,253,346 B2. The identification and quantification of coronaviruses by means of mass spectrometry is taught in U.S. Pat. No. 8,057,993 B2. A hand-held fluorimeter is taught in U.S. Pat. No. 8,269,193 B2.

Diagnosis of COVID-19 may be performed clinically, by detection of SARS-CoV-2, or by measuring SARS-CoV-2 antibody levels in blood. These three methods may produce true positives, false positives, true negatives, false negatives, and indeterminate results. For example, a false negative result may incorrectly indicate that a person is not contagious when, in fact, they are infected.

Clinically, COVID-19 may produce symptoms such as fever, chills, cough, fatigue, loss of appetite, shortness of breath, body aches, nasal congestion, sore throat, nausea, vomiting, diarrhea, persistent chest pain, sudden confusion, stupor, and bluish lips or face within two to fourteen days of exposure to an infected person. Physical signs may include oral temperature above ninety-nine degrees Fahrenheit, decreased oxygen saturation of blood, rales on chest auscultation, and chest computed tomography (CT) findings of ground glass opacities and consolidation, with or without vascular enlargement, septal thickening, and air bronchograms. Clinical diagnosis may require hours or days to produce a result.

Antigen tests for SARS-CoV-2 may be performed on a nasal specimen obtained with swab that is kept in place for ten seconds and twirled three or four times. Done properly, such a procedure should produce tears. Pharyngeal sampling often produces a gag reflex. After collection, swabs are placed in viral transport medium and sent to a clinical laboratory, ideally with refrigeration, requiring hours or days to obtain results using polymerase chain reaction procedures. Point-of-care testing with Abbott ID NOW COVID-19, with FDA emergency use authorization, may provide negative results in as little as 13 minutes. A negative result indicates that a person probably does not harbor SARS-CoV-2 in the nose or throat and is probably not contagious, but recent estimates of false negative results exceed 20%.

Testing for antibodies to SARS-CoV-2 requires a sample of blood obtained by finger stick or venipuncture. Pain and/or anxiety may result from sample collection. Clinical laboratory results may take hours or days to be reported. A rapid point-of-care test is available. A positive result indicates that a person has had COVID-19 at some previous time, has produced an immune response, and is probably not contagious. A negative result does not rule out presence of a communicable state.

SARS-CoV-2 may cause human illness as mild as minor upper respiratory infections (common colds) and as severe as lethal pneumonia, sometimes producing no symptoms at all. It is transmitted by droplets and aerosols of respiratory emissions, mechanical contact, and the fecal-oral route. COVID-19 is a highly contagious viral infection caused by SARS-CoV-2. This novel virus emerged in Wuhan, Hubei Province, People's Republic of China, and became a global pandemic within three months. Case fatality rate, or number of deaths divided by number of infected persons, is presently thought to be 2%. Asymptomatic persons may discharge highly contagious viral particles when they speak. Their hands may transfer coronavirus to surfaces touched by others, widely disseminating an infection.

COVID-19 is so communicable that certain geographic regions sustained numbers of severely ill patients that quickly overwhelmed health care resources such as testing supplies, personal protective equipment, professional personnel, hospital beds, and ventilators. Public health measures of diagnosis, contact tracing, and isolation were rapidly overwhelmed, requiring severe mitigation measures. The Secretary of Health and Human Services (HHS) declared a public health emergency on Jan. 31, 2020, under section 319 of the Public Health Service Act (42 U.S.C. 247d). Initial projections of national fatalities in the range of hundreds of thousands prompted the President of the United States to issue a Proclamation on Declaring a National Emergency Concerning the Novel Coronavirus (COVID-19) Outbreak on Mar. 13, 2020. Entry of certain foreign nationals into the United States was suspended. A task force of experts, led by the Vice President, was convened to advise the President. Nationwide shelter-in-place orders for non-essential occupations resulted in job losses totaling 30 million workers within six weeks, and economic damages totaling trillions of dollars.

As currently instituted mitigation measures are lifted and social interaction increases, COVID-19 remains a threat to public health and safety. A method and apparatus of rapidly screening persons entering schools, places of worship, medical facilities, businesses, airports, arenas, factories, public places, and other venues is needed to protect health and aid economic recovery. A rapid, simple to use, inexpensive, comfortable test performed and/or observed by easily trained persons is needed.

This present invention is designed to enable rapid testing of painlessly obtained saliva samples for the presence of SARS-CoV-2. Compared with a costly nasal swab technique requiring a minimum of 13 minutes to obtain a negative result, this present invention may deliver a result in less than a minute and cost less than a dollar. Greater comfort, speed, and reduced cost are expected outcomes of using this present invention. Adding saliva testing for SARS-CoV-2 to measuring body temperature is expected to increase screening sensitivity and improve public health. Exposing tested samples to certain frequencies of ultraviolet light reduces or eliminates risk of transmitting infection from test materials.

As discussed above, current diagnostic testing for COVID-19 requires nasal and/or throat swabs to collect upper respiratory samples from one or more subjects, causing discomfort and anxiety and consuming resources such as swabs, transport media, and reagents. The most rapid test from Abbott requires a minimum of 13 minutes to produce a negative result. These disadvantages make mass testing impractical for persons seeking entry to places of worship, arenas, stadiums, and airports, for example. This present invention will enable painless specimen collection of saliva, results in less than a minute, and cost less than a dollar.

Detecting SARS-CoV-2 in Biological Samples

The instant disclosure provides, among other things, a method of detecting COVID-19-related virus (e.g., SARS-CoV-2) in a biological sample. In non-limiting embodiments, the method utilizes at least one fluorophore capable of chemically binding with a viral peptide (e.g., spike proteins on SARS-CoV-2) and emitting fluorescence when energized by a light comprising an excitation wavelength for the at least one fluorophore. When mixed with a biological sample, the at least one fluorophore may chemically bind with a viral peptide (e.g., spike proteins on SARS-CoV-2) or any COVID-19-related virus (e.g., SARS-CoV-2) which may exist in the biological sample and, upon being energized by an excitation wavelength, emit fluorescence in a certain wavelength range, which may be detected and identified as a marker of existence of COVID-19-related virus (e.g., SARS-CoV-2) in the biological sample.

Fluorophores

Fluorophores described herein may include any fluorophores capable of chemically binding with a viral peptide. In non-limiting embodiments, fluorophores described herein are capable of chemically binding with a tetracysteine sequence (e.g., two cysteine pairs separated by certain amino acid residues) in a viral peptide. In some embodiments, fluorophores described herein include biarsenical compounds, such as biarsenical dyes, such as ReAsH-EDT$_2$, ReAsHO, HoXAsH-EDT$_2$, CHoXAsH-EDT$_2$, FlAsH-EDT$_2$, 5/6-CrAsH-EDT$_2$, AF568-FlAsH, Biotin-FlAsH (Bio-FlAsH), β-alanyl FlAsH, AsCy3, CrAsH-EDT$_2$, sFlAsH-EDT$_2$, F2-FlAsH-EDT$_2$, SpLAsH-EDT$_2$-Alexa594, CaG FlAsH-EDT$_2$, AsCy3-EDT$_2$, etc., including a chemically acceptable salt or precursor thereof, comprising the structure of Formula I, II, III, or other structures described in the instant application or known by a skilled artisan. Such known fluorophores may include those described in Adams et al., *J. Am. Chem. Soc.* (2002) 124:6063-6076; Gaspersic et al., *FEBS J.* (2010) 277:2038-2050; Taguchi et al., *Molecular Biology of the Cell* (2009) 20:233-244; Thorn et al., *Protein Science* (2000) 9:213-217; and Alexander and Schepartz, *Org. Lett.* (2014) 16:3824-3827. In some embodiments, the fluorophores described herein include FlAsH-EDT$_2$ or ReAsH-EDT$_2$. Table 1 and the quotation below (from Adams et al., *J. Am M. Chem. Soc.* (2002) 124:6063-6076, incorporated herein by reference to its entirety) compare relative efficiency of the fluorescent staining of tetracysteine-tagged gap junctions and subsequent photoconversion of 3,3'-Diaminobenzidine by biarsenical dyes (EDT bound). One exemplary dye, FlAsH-EDT$_2$, "is practically nonfluorescent but becomes more than 50,000 times more fluorescent (quantum yield ≈0.5) upon exchanging the EDTs for a tetracysteine-containing peptide. Presumably FlAsH-EDT$_2$ is quenched by vibrational deactivation or photoinduced electron-transfer mechanisms, which are hindered by the more rigid and constrained peptide complex. This enhancement is very valuable because it reduces the need to remove excess FlAsH-EDT$_2$ rigorously" (see Table 1 and comments in Adams et al.).

TABLE 1

Comparison of Biarsenical Dyes

| name | W | X | Y | Z | fluorescent staining efficacy | DAB photoconversion efficacy |
|---|---|---|---|---|---|---|
| FlAsH | H | H | O | C—C$_6$H$_4$COOH | ++++ | – |
| BrAsH | Br | H | O | C—C$_6$H$_4$COOH | +++ | + |
| Br$_2$AsH | Br | Br | O | C—C$_6$H$_4$COOH | ++ | ++ |
| tFlAsH | H | H | S | C—C$_6$H$_4$COOH | (+) | – |
| ReAsH | H | H | O | N | ++++ | +++ |
| Br$_2$ReAsH | Br | Br | O | N | ++ | +++(+) |
| ThAsH | H | H | S | N | – | – |

Fluorophores described herein may be energized by absorbing a light comprising an excitation wavelength range (maximal at a certain wavelength $\lambda_1$) and, upon being energized, emit fluorescence at an emission wavelength range (maximal at a certain wavelength $\lambda_2$). Thus, when bound to any COVID-19-related virus (e.g., SARS-CoV-2) in a biological sample, a fluorophore may absorb and be energized by a light comprising a wavelength range (maximal at $\lambda_1$) and emit a wavelength range (maximal wavelength at $\lambda_2$). Detection of the emitted wavelength range (maximal wavelength at $\lambda_2$) may help to detect SARS-CoV-2 in a biological sample. In some embodiments, more than one fluorophore may be used for such virus detection. For example, a first fluorophore having an excitation wavelength range (maximal wavelength at $\lambda_1$) and an emission wavelength range (maximal wavelength at $\lambda_2$) may be combined with a second fluorophore capable of being energized by the energized first fluorophore and having an emission wavelength range (maximal wavelength at $\lambda_3$) for detection. In some embodiments, the first fluorophore, when bound with the viral peptide target, is capable of being energized by an excitation wavelength range (maximal wavelength at $\lambda_1$). Rather than emitting fluorescence, the energized first fluorophore may transfer a part or all of its energy to the second fluorophore, thus energizing the latter to emit fluorescence at its emission wavelength range (maximal wavelength at $\lambda_3$), which may be detected. In some embodiments, Forster or fluorescence resonance energy transfer (FRET) may be formed between the first and the second fluorophores. Alternatively, the energy may be transferred indirectly between the first and the second fluorophores.

Viral Peptide Target

Figure 4:
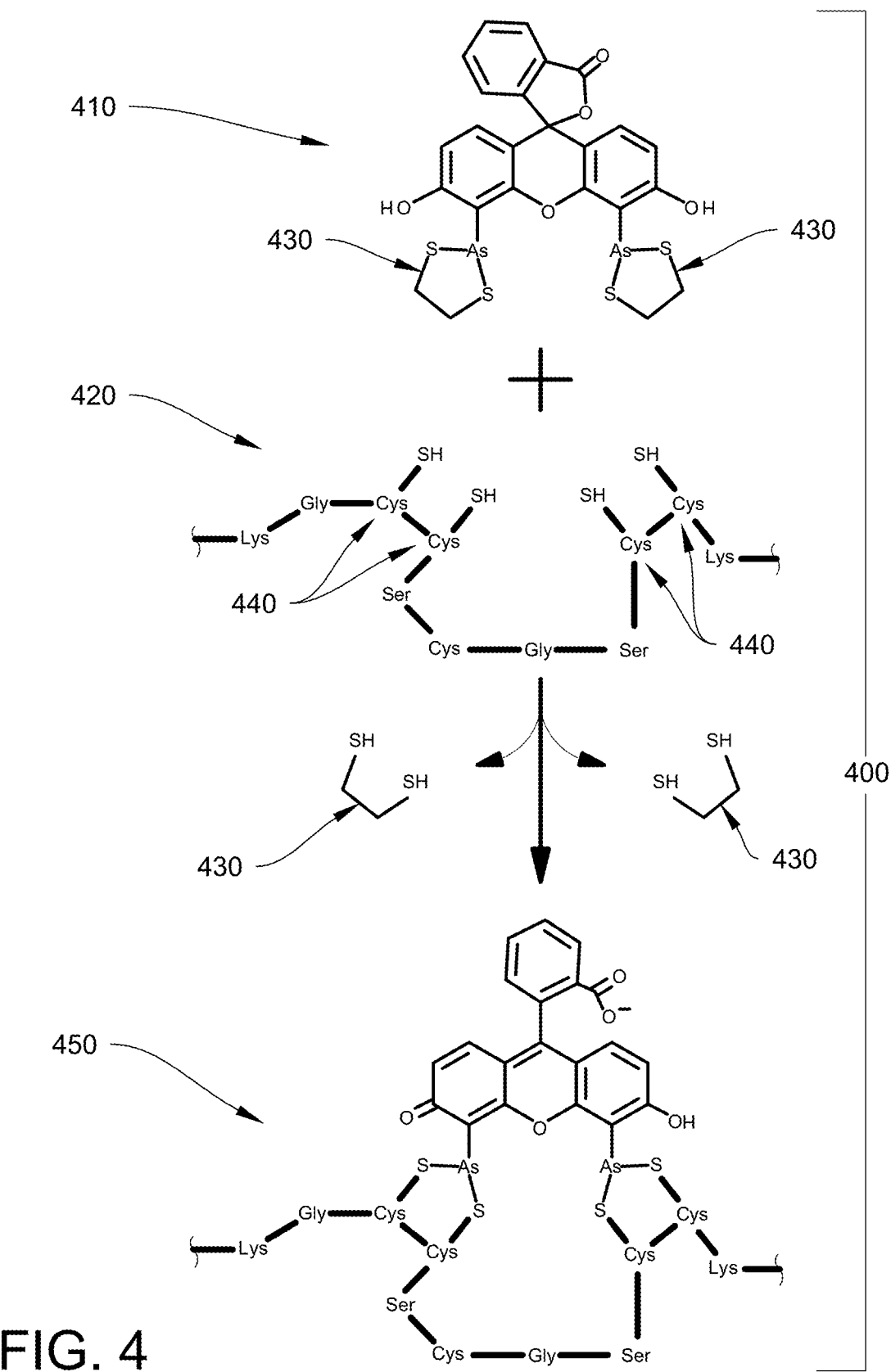
FIG. 4 is a graph schematically illustrating a non-limiting example of a chemical reaction 400 that combines a FlAsH-EDT$_2$ fluorophore 410 with an eleven amino acid peptide segment ("K9K peptide") 420 of the SARS-CoV-2 spike protein from position 1245 to 1255 (i.e., in the direction from the N terminus to the C terminus, KGCCSCGSCCK; SEQ ID NO: 3).

Viral peptide target for binding with the fluorophores described herein may include any viral peptide of a COVID-19-related virus (e.g., SARS-CoV-2 spike proteins). In non-limiting embodiments, such peptide target comprises a tetracysteine sequence (e.g., two cysteine pairs separated by certain amino acid residues), such as C$_1$C$_2$X$_n$C$_3$C$_4$(SEQ ID NO: 1), wherein C$_1$-C$_4$ refer to four cysteine residues, X$_n$ refers to any number (n) of amino acid residue(s), and n is an integer selected from 1 to 29. In some embodiments, n is selected from 1, 2, 3, 4, 5, 6, 7, 8, 9, 10, 11, 12, 13, 14, 15, 16, 17, 18, 19, 20, or more. In some embodiments, n is 1, 2, or 4. For example, when a fluorophore binds to a tetracysteine sequence on a single SARS-CoV-2 spike protein strand, n may be 3, 4, 5, 10, 11, or 16. While a fluorophore binds to two cysteine pairs localized on different spike protein strands, n does not apply. In some embodiments, the tetracysteine sequence described herein comprises CCSCGSCC (SEQ ID NO: 2). In some embodiments, the viral peptide target comprises amino acid residues 1245-1255 (from N-terminus to C-terminus, KGCCSCGSCCK; SEQ ID NO: 3; referred to "K9K peptide" in this application) of the SARS-CoV-2 spike protein. Because SARS-CoV-2 has about 100 spike protein trimers (each having 3 copies of spike protein strands) anchored to its viral membrane, each virus would have about 300 copies of the K9K peptide target for recognition by fluorophores, which could contribute to the quick and efficient detection of the virus described herein. A model showing the chemical binding of a fluorophore (e.g., FlAsH-EDT$_2$) and a K9K peptide target is shown in FIG. 4.

Optional Methods

The methods for detection described herein and the compositions for the same further can include the use of a reducing agent and/or heat. Without being limited, in some cases, the inclusion of the reducing agent and/or heat can improve the speed of detection, the sensitivity or various other factors. In some embodiments, the methods and compositions for detection described herein further can include a reducing agent. Non-limiting examples of reducing agents may include tris(2-carboxyethyl)phosphine (TCEP), British anti-Lewisite (BAL, a.k.a., dimercaprol), 2-aminoethanethiol (cysteamine), cysteine, dithiobutylamine (DTBA), dithioerythritol (DTE), dithiothreitol (DTT), glutathione, β-mercaptoethanol (β-ME), sodium 2-mercaptoethanesulfonate (MESNa), or their chemically acceptable salts. Experiments showing improvement in the methods and compositions using a reducing agent are presented in the Examples.

In some embodiments, the method described herein further can include heating the composition for detection to at least a temperature $T_1$, prior to the measuring in step iii) or iv). In some embodiments, the temperature $T_1$ may be at least about 15° C., 20° C., 25° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., or higher. In some embodiments, the temperature $T_1$ may be at least about 40° C. The heat can be applied by any suitable method. In some embodiments, the heating is provided by a heating element. The detection device can include a heating element. Experiments showing improvement in the methods and compositions using heat are presented in the Examples.

Example Systems and Devices Apparatuses

Non-limiting example systems for collecting a biological sample and/or detecting SARS-CoV-2 in a biological sample are shown in FIGS. 1-3 and 5-7. The biological sample described herein may include a body fluid of one or more subjects, or is selected from a group consisting of saliva, oral fluid, or nasal drainage fluid, nasal swab residue, nasopharyngeal swab residue, pharyngeal swab residue, upper and/or lower respiratory tract aspirate, and stool. The one or more subjects may be human, non-human mammal, non-mammal animal, pet, dog, cat, cow, pig, sheep, chicken, bird, bat, rabbit, or any animal to be tested for virus. The exemplary systems may further contain other devices as described herein, such as an emitter, a detector, an optical device to reflect energizing light a plurality of times through the biological sample, a device to stimulate production of the biological sample, a heater to heat the biological sample, a filter to remove debris, cells, and/or tissues in the biological sample, a viral selective surface or membrane to adhere SARS-CoV-2, a centrifuge to concentrate SARS-CoV-2, etc.

An exemplary device to stimulate production of the biological sample may include a salivation stimulating scented sticker, comprising a pad saturated with a volatile scent that is emitted through perforations in a covering sheet. Said scent may resemble food materials that stimulate saliva production in anticipation of eating.

An example sample collector may comprise a structure into which one or more test subjects deposit saliva. Examples of the sample collector include, but are not limited to, a spoon, test tube, cuvette, syringe, slide, and cup. The sample collector may incorporate one or more materials that include, but are not limited to, angiotensin converting enzyme 2, heparin, and heparan sulfate proteoglycans to enhance adhesion of material, and/or components thereof, being tested.

An exemplary filter may comprise a porous membrane that allows passage of the saliva while obstructing passage of food particles, debris, cells, bacteria, yeast and any material adverse to the testing process for SARS-CoV-2. Examples of the filter include, but are not limited to, a syringe filter with a membrane porosity of 0.22 or 0.45 microns, diameter of 25-50 mm, and filter material such as polyethersulfone (PES) or polyvinylidene fluoride (PVDF), or any suitable material that does not inhibit the passage of virus, with or without a glass fiber prefilter.

An exemplary pre-fluorescent dye may comprise an organic chemical compound that binds to an appropriate or desired region of the virus or a viral antigen, including, for example, various cysteine-containing sequences, some of which are similar to the specific one in SARS-CoV-2 spike protein's cysteine-rich region. Any suitable fluorophore may be utilized, including those described elsewhere herein. Examples of said dye include FlAsH-EDT2 (also known as Lumio Green), available from Caymen Chemical Item 20704, that absorbs light energy with a maximum at 508 nanometers (nm) and emits fluoresence with a maximum at 528 nm, or ReAsH-EDT2 (also known as Lumio Red), available from Caymen Chemical Item 19767 that absorbs light energy at 593 nm and emits fluorescence at 608 nm.

An exemplary analyzer may comprise a light source, an optional excitation filter positioned between the light source and a test sample, an emission detector positioned within or outside the test sample, an optional emission filter positioned between said emission detector and said test sample, hardware and software to interpret the emission that is detected, and means of displaying the result. The analyzer may comprise one or more reflecting surfaces which cause said emission to pass through said test specimen a plurality of times. In a preferred embodiment, a hand-held analyzer comprises one or more diodes that generate light waves that will interact with the spike protein of SARS-CoV-2 after a fluorescent dye has been attached.

Some embodiments herein relate to devices or apparatuses that can be used with the methods for detection described herein.

Figure 5:
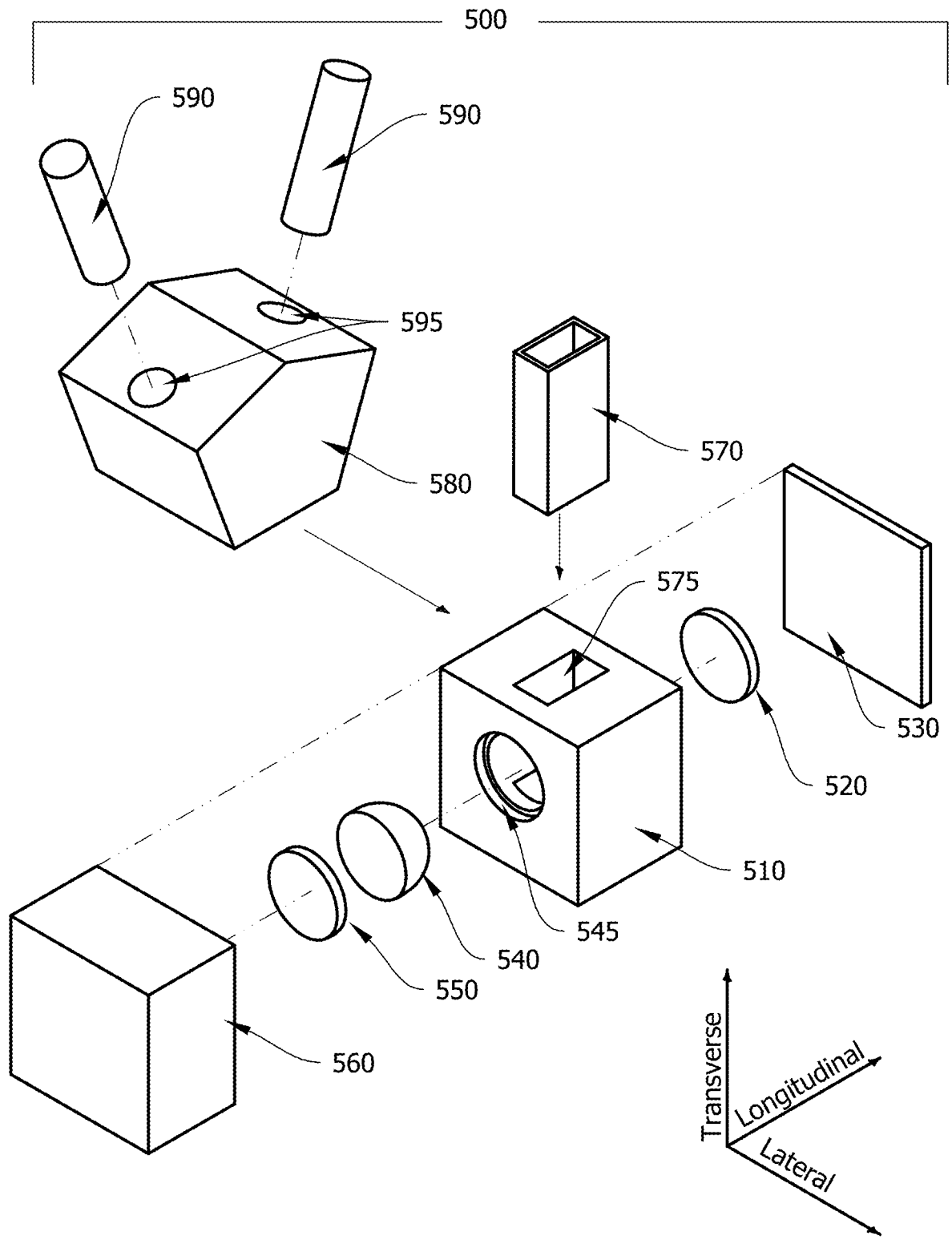
FIG. 5 is a graph schematically illustrating a top perspective exploded view of a non-limiting example of an analyzer 500.

FIG. 5 is a graph schematically illustrating a top perspective exploded view of a non-limiting example of an analyzer 500. The specimen body 510 holds a concave emission mirror 520 and an optical condenser 540 which seats in a condenser recess 545. A back plate 530 retains the concave emission mirror 520 in position. The concave emission mirror 520 receives fluorescence from a specimen and reflects it toward the optical condenser 540. Said fluorescence then passes through an emission filter 550 into a spectrometer body 560. A cuvette 570 holds approximately 7 milliliters of a specimen for analysis. Said cuvette 570 is placed into a cuvette chamber 575 by an operator. A laser holder 580 contains two lasers 590 that are inserted into laser chambers 595. Said lasers are thereby aimed such that their light beams (695 in FIG. 6B) pass diagonally through the cuvette chamber 575 to irradiate the maximum possible amount of a specimen. After the cuvette 570 is inserted into the cuvette chamber 575, the laser holder 580 is placed on top of the specimen body 510 and the lasers 590 are activated.

Figure 6A:
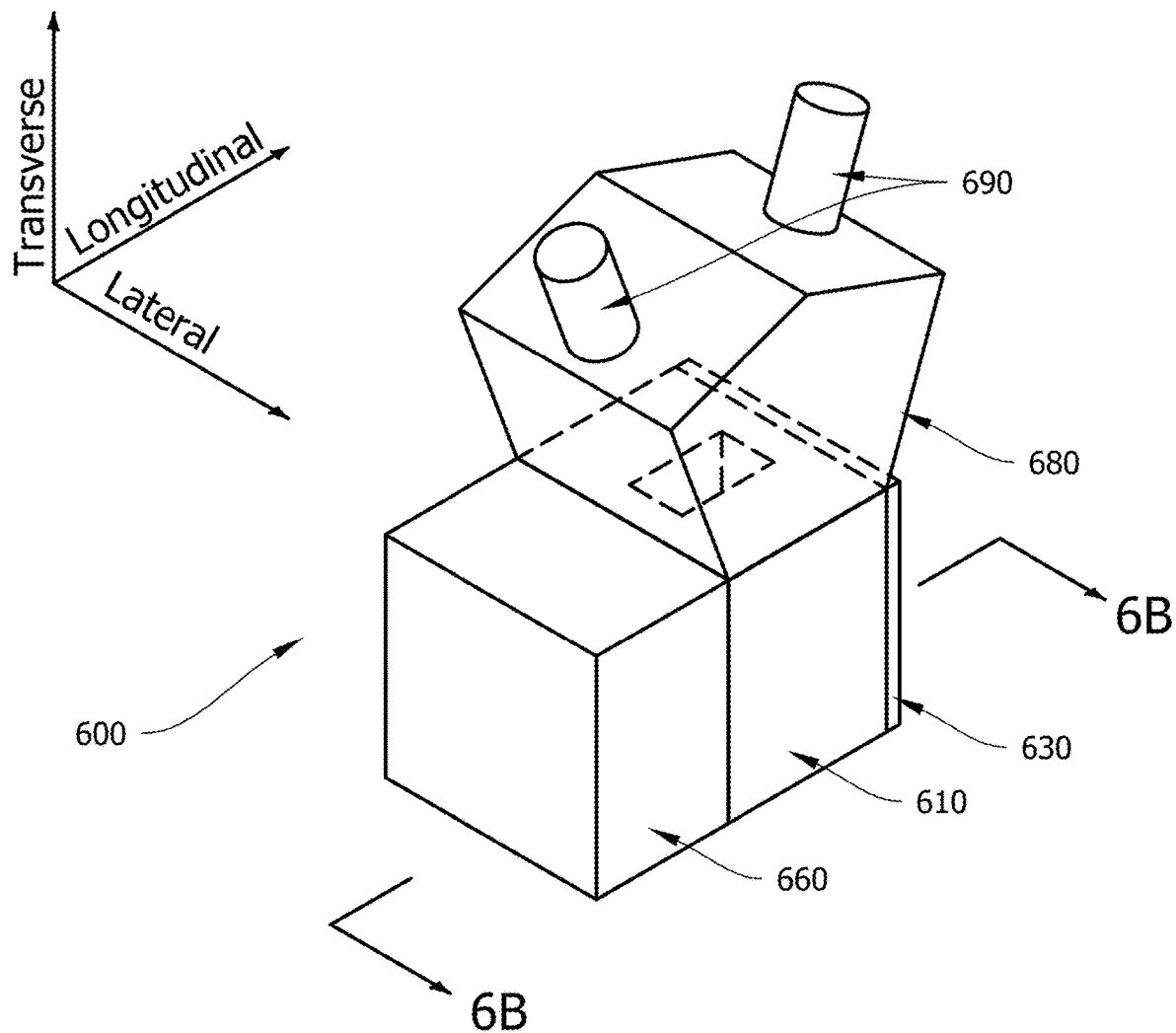
FIGS. 6A-6B are a set of graphs schematically illustrating a non-limiting example of an assembled analyzer 600.
Figure 6B:
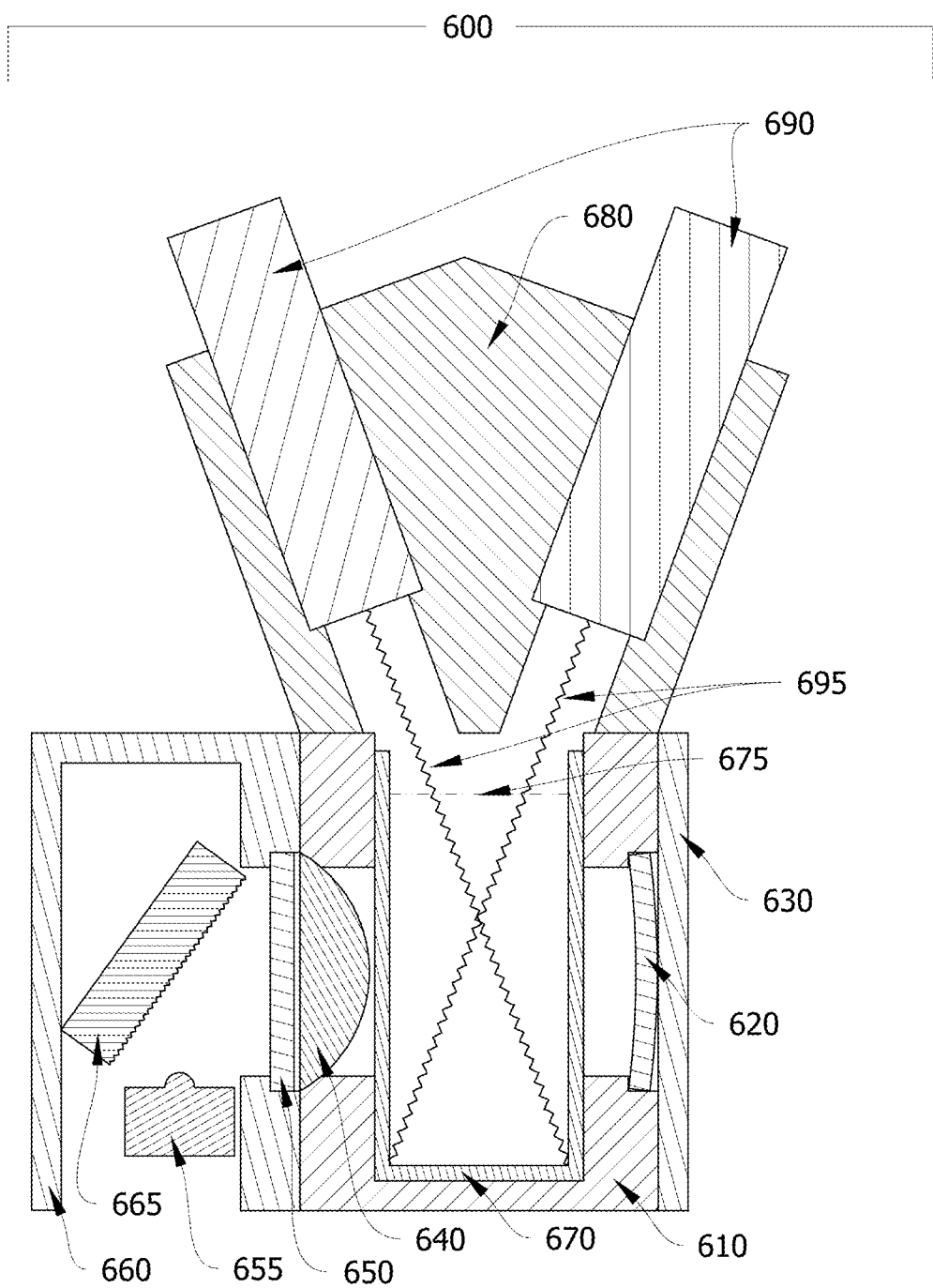

FIGS. 6A-6B are a set of graphs schematically illustrating a non-limiting example of an assembled analyzer 600. FIG. 6A illustrates a top perspective view. It can be seen that a back plate 630 has been affixed to a specimen body 610, thereby securing a concave emission mirror (520 in FIG. 5) in proper position. Two lasers 690 have been inserted into a laser holder 680, which has been movably placed on top of a specimen body 610. A spectrometer body 660 has been affixed to the specimen body 610, thereby securing an optical condenser (540 in FIG. 5) and an emission filter (550 in FIG. 5) in proper position. FIG. 6B illustrates an orthogonal sectional lateral view. It can be seen that a cuvette 670 is present in a specimen body 610, and a sample fluid level 675 is visible. In usage, a laser body 680 is placed directly on top of the specimen body 610. Two lasers 690 generate light beams 695 that pass diagonally across the interior of the cuvette 670, irradiating a maximum amount of sample. Fluorescence generated by a fluorophore bound to tetracysteine (450 in FIG. 4) is emitted in all directions. A portion of said emissions pass through an optical condenser 640 and emission filter 650, striking a diffraction grating 665 and spectrally spreading at an angle toward a photon detector 655 within a light tight spectrometer body 660. Said photon detector 655 may include, but is not limited to, a charge coupled device (CCD) or complementary metal oxide semiconductor (CMOS) sensor. A portion of said emissions directed away from the optical condenser 640 strike a concave emission mirror 620 and are reflected toward and through the optical condenser 640, thereby increasing sensitivity of the analyzer 600. The concave emission mirror 620 is held in place and stabilized by a light tight back plate 630.

Figure 7A:
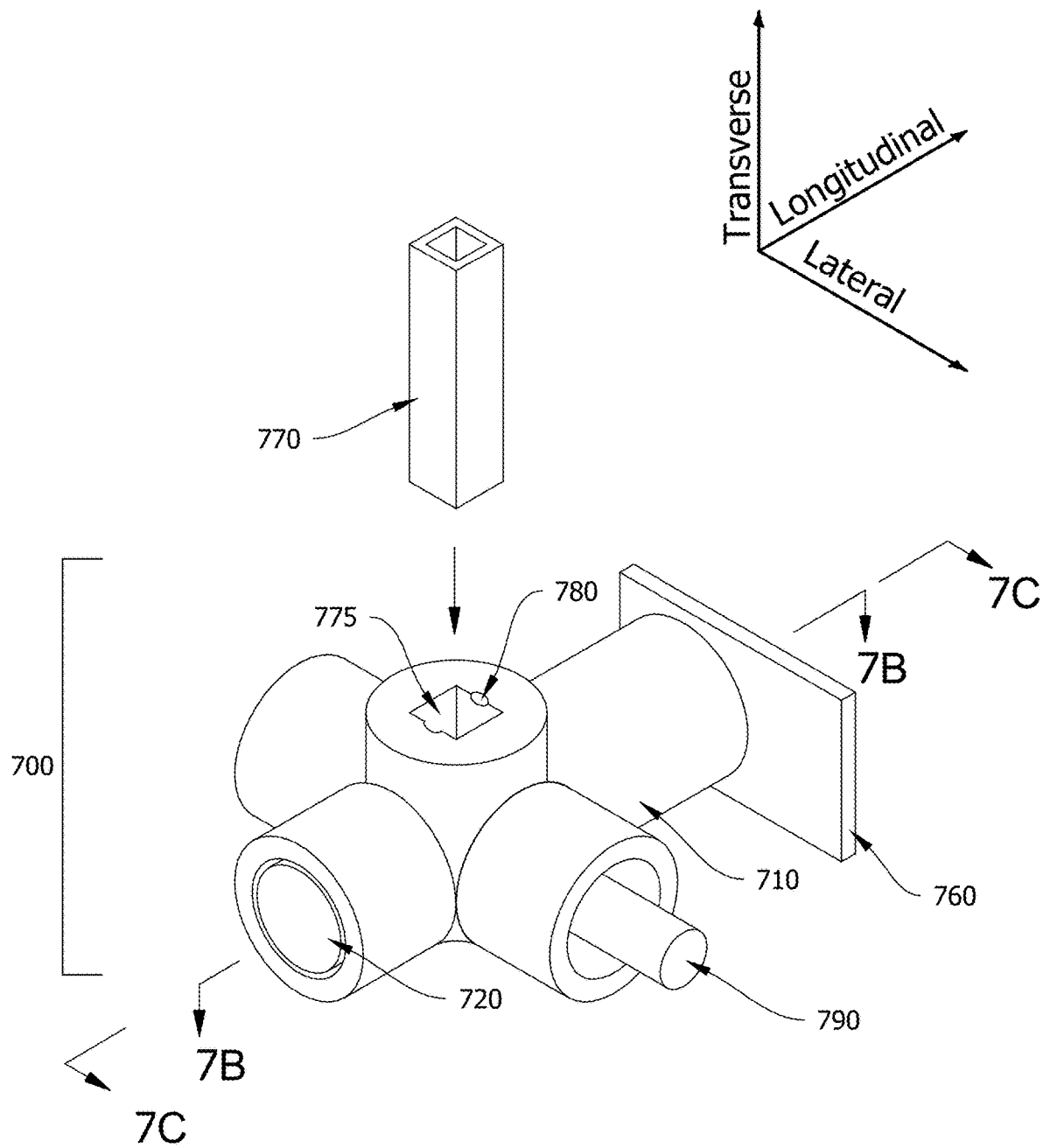
FIGS. 7A-7C are a set of graphs schematically illustrating a non-limiting example of an analyzer 700 and a cuvette 770.
Figure 7B:
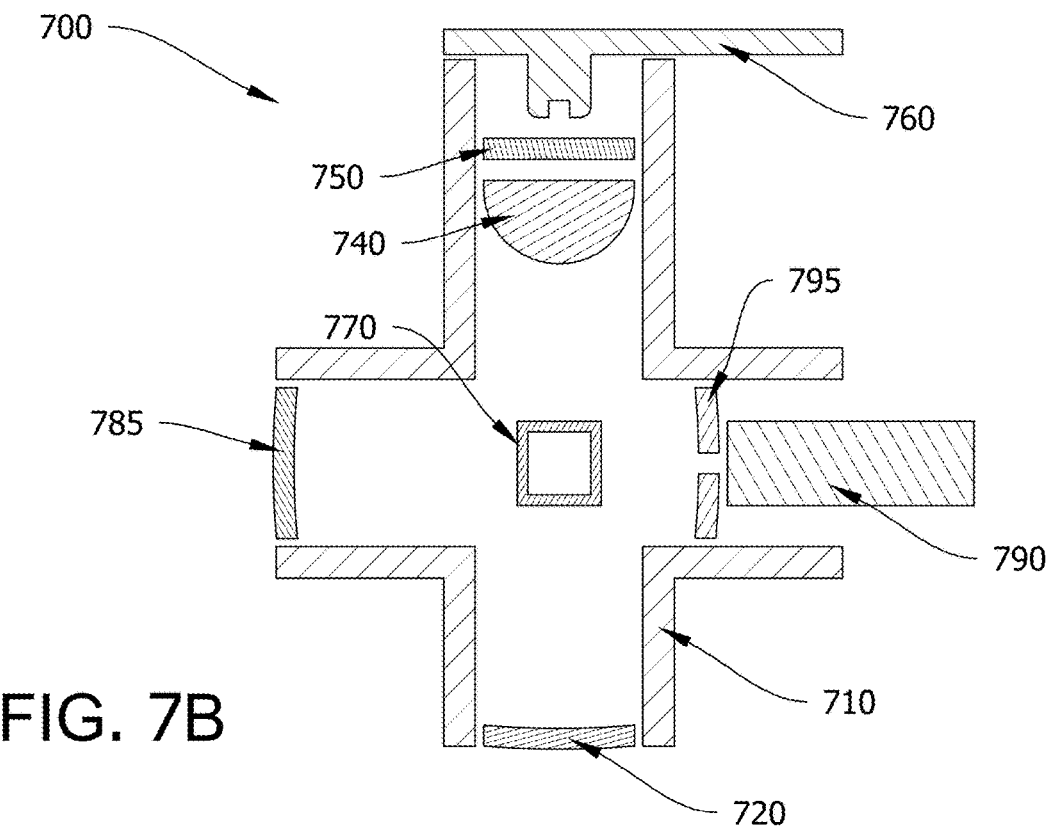
Figure 7C:
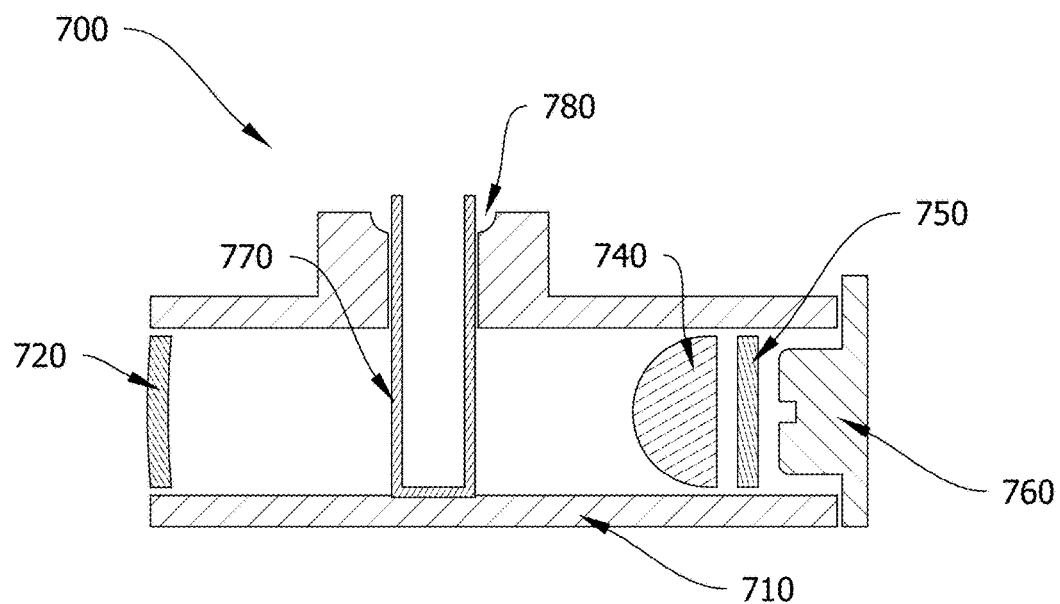

FIGS. 7A-7C are a set of graphs schematically illustrating a non-limiting example of an analyzer 700 and a cuvette 770. FIG. 7A illustrates a top perspective view. The analyzer body 710 comprises a concave emission mirror 720 that reflects fluorescence from a specimen toward an optical condenser (not seen) and through an optional emission filter (not seen) into a microspectrometer 760. A cuvette 770 holds approximately 3 milliliters of a specimen for analysis. In usage, the sample for analysis is placed into the cuvette 770 which is placed into a cuvette chamber 775 by an operator. A laser 790 irradiates the sample in the cuvette 770 within the cuvette chamber 775. A recess 780 in the analyzer body 710 allows the cuvette 770 to be conveniently removed from the cuvette chamber 775. FIG. 7B illustrates an orthogonal sectional top view. It can be seen that a cuvette 770 is present in an analyzer body 710. A laser 790 is aimed at the cuvette 770 through a central hole in a concave mirror 795. A concave laser mirror 785 is positioned opposite the laser to reflect irradiation back through the cuvette 770. Said opposing mirrors 785 and 795 cause energizing light to pass through the cuvette 770 a plurality of times, thereby increasing the possibility of fluorescence by a sample. A portion of said fluorescence at a right angle to a laser beam passes directly through an optical condenser 740 and emission filter 750 into a microspectrometer 760. A portion of said fluorescence emanating away from the optical condenser 740 strikes a concave emission mirror 720 and is reflected back toward and through the optical condenser 740, thereby increasing sensitivity of the analyzer 700. FIG. 7C illustrates an orthogonal sectional lateral view. It can be seen that a cuvette 770 is present in an analyzer body 710. Access to the top of the cuvette 770 is facilitated by a recess 780 in the analyzer body 710. A portion of fluorescence at a right angle to a laser beam passes directly through an optical condenser 740 and emission filter 750 into a microspectrometer 760. A portion of said fluorescence emanating away from the optical condenser 740 strikes a concave emission mirror 720 and is reflected back toward and through the optical condenser 740, thereby increasing sensitivity of the analyzer 700. Some embodiments herein relate to devices or apparatuses for detecting a light or energy emission, including emissions as described herein to detect the presence of a SARS-CoV-2 infection. The devices can include or more, two or more, three or more, etc. of the components described herein. Those components can improve the sensitivity of the detection in some cases. For example, the devices can include any one or more of the FIGS. 5-7, such as, the particular cuvettes, one or more of the described mirrors, one or more of the lasers with one or more of them configured or angled as described, one or more of the condensers, a heating element, and the like (any one or more of the components 500-770, without limitation. In some cases, the one or more components described in FIGS. 5-7 can incorporated into an existing device or fluorimeter. Some embodiments relate to methods of detecting (e.g., SARS-CoV-2) utilizing a device or apparatus as described herein with any of the methods set forth herein, including the methods described in the Summary of the Invention, the detailed description and the claims as filed.

In usage, the sample collector is removed from an enclosure or protective packaging that prevents it from becoming contaminated. The one or more test subjects rubs a salivation stimulating sticker that may be attached to said collector and sniffs the scent. Said subject(s) then deposits saliva into said collector in sufficient quantity for analysis and hands it to an operator. Said operator then draws a portion or all of said saliva sample into a syringe and attaches said syringe to a syringe filter. In a preferred embodiment, a syringe comprises a funnel shaped opening that tapers to a typical syringe barrel, permitting insertion of the syringe plunger, thereby eliminating the need to collect saliva in a separate cup and draw it into a syringe. The operator then applies pressure to the syringe plunger forcing the saliva through the filter into a test tube. A drop of solution of fluorescent dye or pre-fluorescent substance that bonds chemically to the spike protein on SARS-CoV-2 is added, and the tube is shaken to mix the contents and promote chemical reaction. In a preferred embodiment, said fluorescent dye or pre-fluorescent substance has been pre-deposited in said test tube. The test tube is then placed into a guide in the analyzer that positions the saliva sample in a path of irradiation. The analyzer is then closed or covered by means to prevent ambient light from entering. An LED or other suitable emitter, with or without a filter, generates light at a frequency known to be absorbed by the fluorophore-viral protein compound. Employing one or more solid state sensors, with or without a filter or filters, the analyzer measures emitted fluorescence produced by the fluorophore-viral protein compound. The analyzer reports presence or absence of virus by means that include, but are not limited to, sound, light, digital display, meter, and vibration. Ultraviolet light, typically 254 nm, may be applied to the sample after testing in order to achieve a germicidal effect. The test tube is removed from the analyzer and disposed of in a sanitary manner, or safely stored for cleaning and disinfecting for later reuse. Biodegradable sample collectors are used when possible to minimize negative environmental impact. The analyzer is cleaned periodically to avoid contamination and interference with subsequent test results.

In an example of a prospective airline passenger during a COVID-19 pandemic, a test result that is free of SARS-CoV-2 (a negative result) will permit a passenger to proceed. If SARS-CoV-2 is detected (a positive result) an alternative form of testing may be offered or medical attention advised.

EXAMPLES

Experiments related to fluorophore binding and fluorescence detection were performed.

FIG. 4 is a graph schematically illustrating a non-limiting example of a chemical reaction 400 that combines a FlAsH-EDT$_2$ fluorophore 410 with an eleven amino acid peptide ("K9K peptide") 420 identical to the SARS-CoV-2 spike protein amino acid sequence from position 1245 to 1255 (i.e., KGCCSCGSCCK; SEQ ID NO: 3). It will be seen that the EDT moieties 430 are replaced by the cysteine amino acids 440 within the spike protein peptide segment 420. The reaction product 450 is capable of absorbing light and emitting fluorescence.

Figure 8:
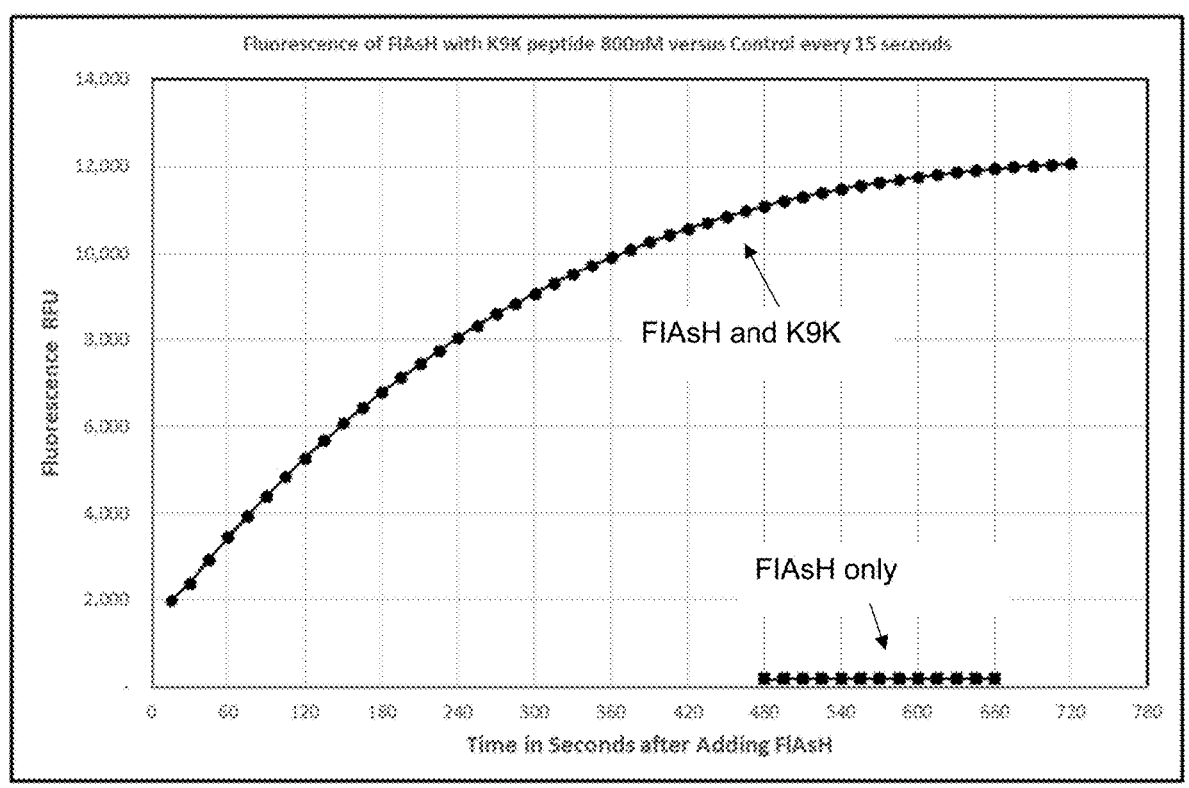
FIG. 8 is a graph schematically illustrating that emission of fluorescence by FlAsH, when bound to the K9K peptide target, begins within 15 seconds (the upper curve, each dot represents a fluorescence reading at a time point). FlAsH only was used as control (the lower line, each box represents a fluorescence reading at a time point).

FIG. 8 shows emission of fluorescence by FlAsH, when bound to the K9K peptide target. FIG. 8 is a graph schematically illustrating that emission of fluorescence by FlAsH, when bound to the K9K peptide target, begins within 15 seconds. K9K peptide at a final concentration of 800 nM was treated with the fluorophore FlAsH-EDT$_2$ and irradiated at 470 nm, and the emitted fluorescence was measured every 15 seconds. The x-axis of the graph represents time (in seconds) after mixing the fluorophore and the K9K peptide, while they-axis represents the intensity of emitted fluorescence (in relative fluorescence units (RFU)), measured in a Thermo Fisher Qubit 4 Fluorometer. Fluorophore only, without the K9K peptide, was used as control. This demonstrates the rapid detection by the methods and the systems described herein.

Figure 9:
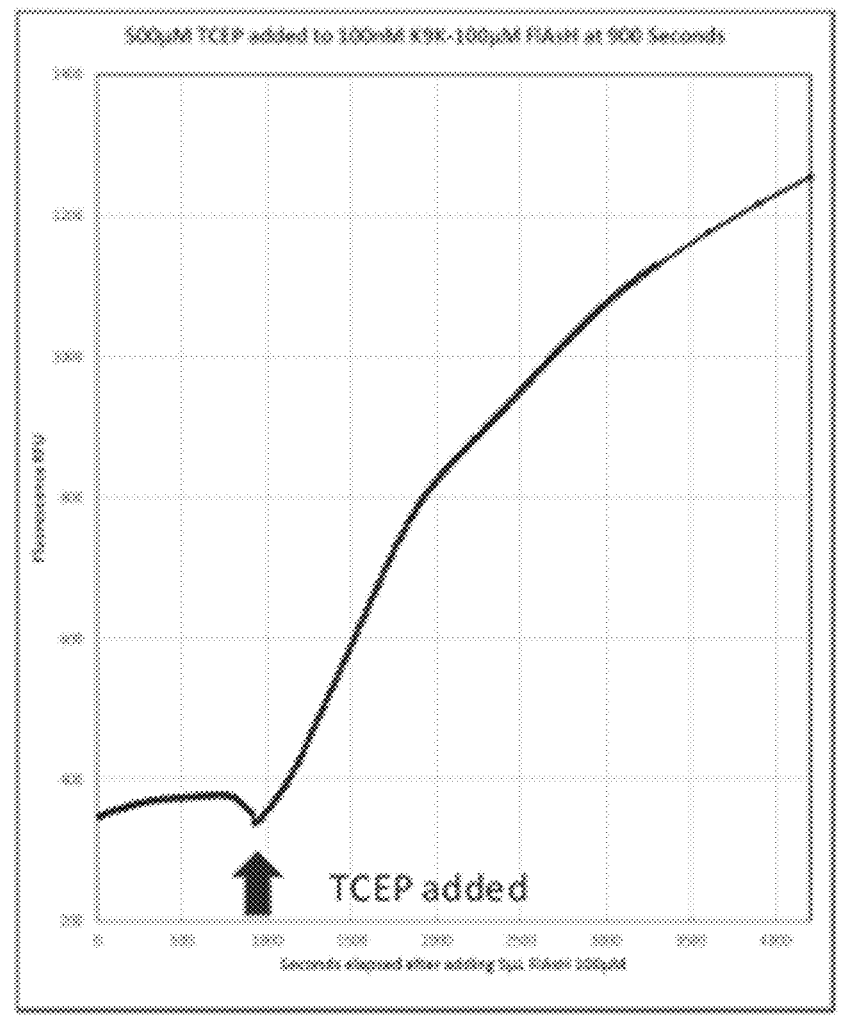
FIG. 9 is a graph schematically illustrating that emission of fluorescence by a fluorophore, upon being bound to the target peptide, can be enhanced by addition of a reducing agent.
Figure 10:
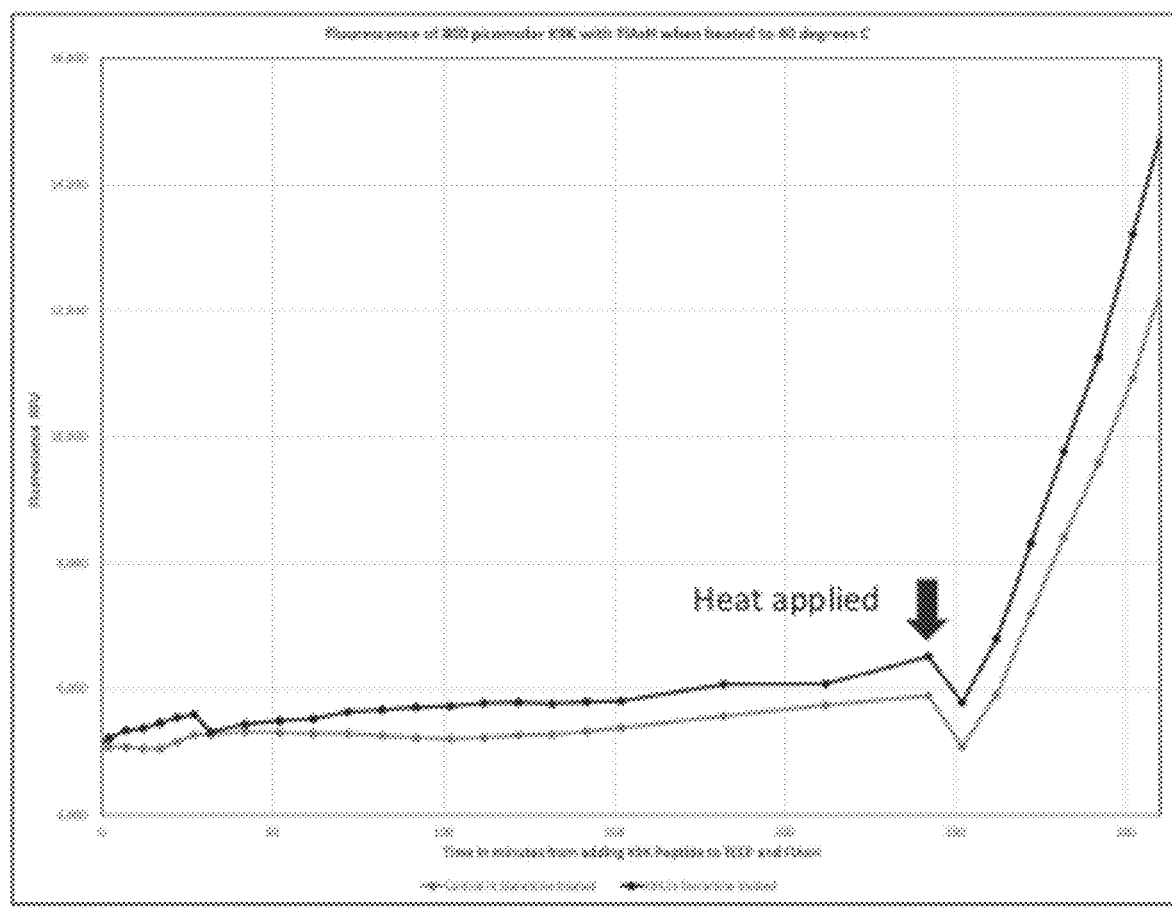
FIG. 10 is a graph schematically illustrating that emission of fluorescence by a fluorophore, upon being bound to the target peptide, can be enhanced by heating the mixture.

The emitted fluorescence may be enhanced by addition of reducing agents to the fluorophore-K9K peptide mixture in the biological sample (FIG. 9) or heating the biological sample to, e.g., about 40° C. (FIG. 10). FIG. 9 is a graph schematically illustrating that emission of fluorescence by a fluorophore, upon being bound to the target peptide, can be enhanced by addition of a reducing agent. At 900 seconds after mixing K9K peptide (final concentration about 100 nM) and FlAsH-EDT$_2$ (final concentration about 1 µM) in a neutral pH HEPES buffer, when fluorescence levels were stable, TCEP (final concentration about 50 µM) was added to the mixture. The emitted fluorescence was measured using the same methods as for FIG. 8.

FIG. 10 is a graph schematically illustrating that emission of fluorescence by a fluorophore, upon being bound to the target peptide, can be enhanced by heating the mixture. K9K peptide (at a final concentration of 800 µM) was treated with the fluorophore FlAsH-EDT$_2$ and the emitted fluorescence, after the fluorophore was excited by an energizing light, was measured using the same methods as for FIG. 8. After 4 hours of stable fluorescence measurements, the mixture of the peptide and the fluorophore was heated to 40° C. The upper line represents the mixture of the K9K peptide and the fluorophore and the lower line represents a control sample. Fluorescence more than doubled over the next hour.

Figure 11:
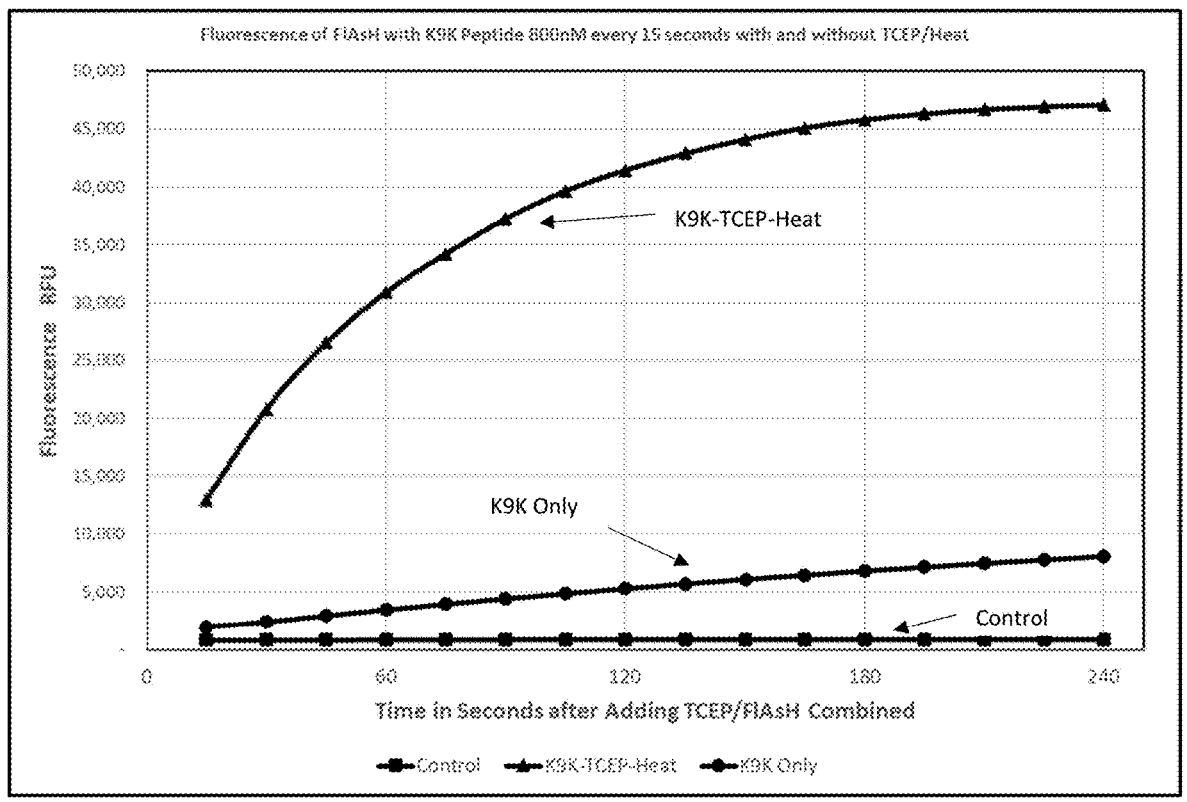
FIG. 11 is a graph schematically illustrating that emission of fluorescence by a fluorophore, upon being bound to the target peptide, can be enhanced by addition of a reducing agent and heating the mixture.

Combination of reducing agents and heating greatly improved the emission fluorescence signal (FIG. 11). FIG. 11 is a graph schematically illustrating that emission of fluorescence by a fluorophore, upon being bound to the target peptide, can be enhanced both by addition of a reducing agent and by heating the mixture. K9K peptide (at a final concentration of 800 nM) was treated with the fluorophore FlAsH-EDT$_2$ and then with TCEP and heated as in FIGS. 9 and 10. The emitted fluorescence, after the fluorophore was excited by an energizing light, was measured as in FIG. 8, for the first four minutes. Said mixture was compared with K9K peptide at the same concentration treated with fluorophore but without TCEP or heating. The fluorophore was used as a control. Within four minutes after addition of FlAsH to the K9K peptide, fluorescence was nearly six times greater in the sample with TCEP and heating.

Figure 12:
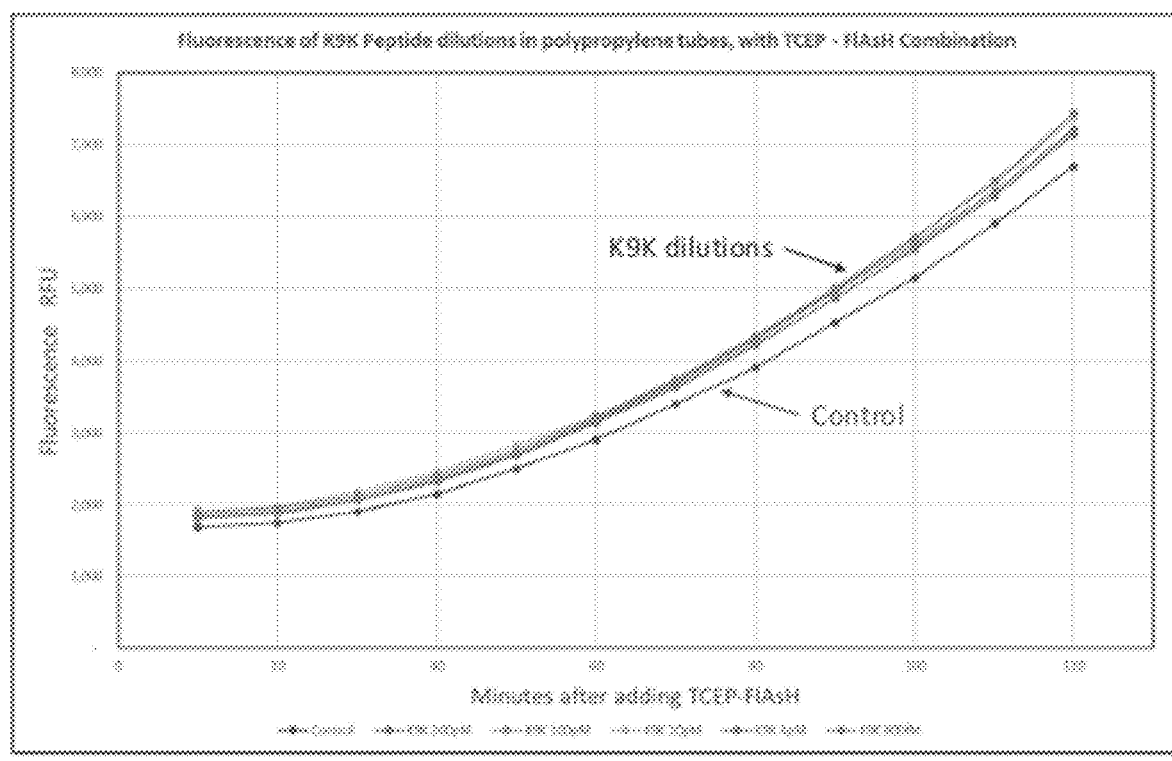
FIG. 12 is a graph schematically illustrating emission of fluorescence by a fluorophore, upon being bound to various concentrations of the target peptide.
Figure 13:
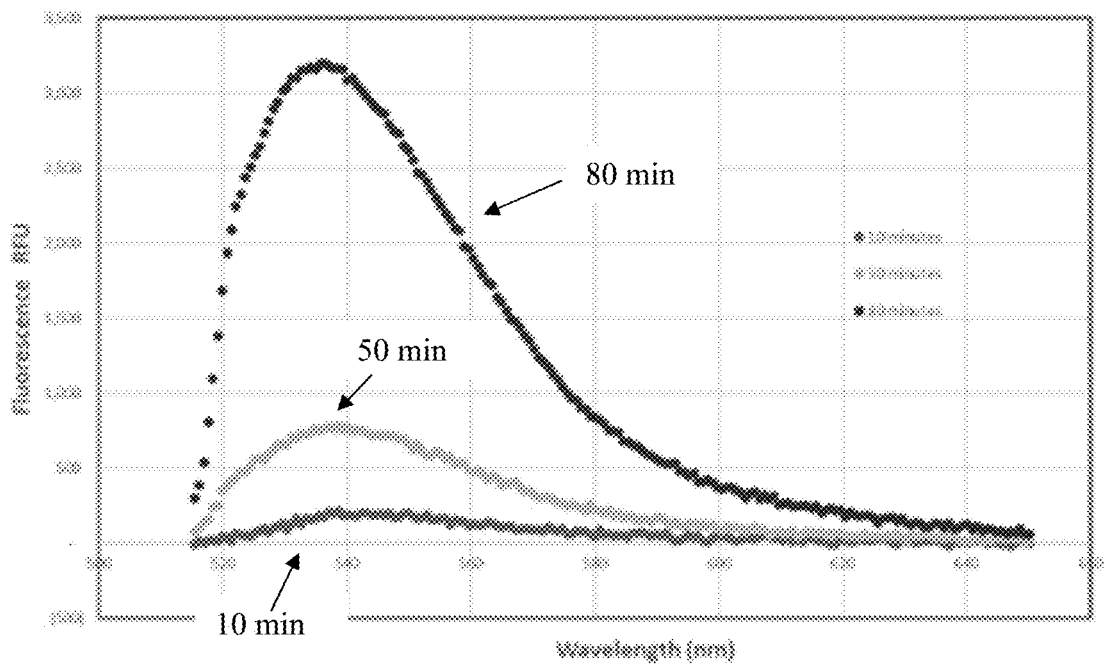
FIG. 13 is a graph schematically illustrating emission of fluorescence by a fluorophore, upon being bound to various concentrations of the target peptide.
Figure 14:
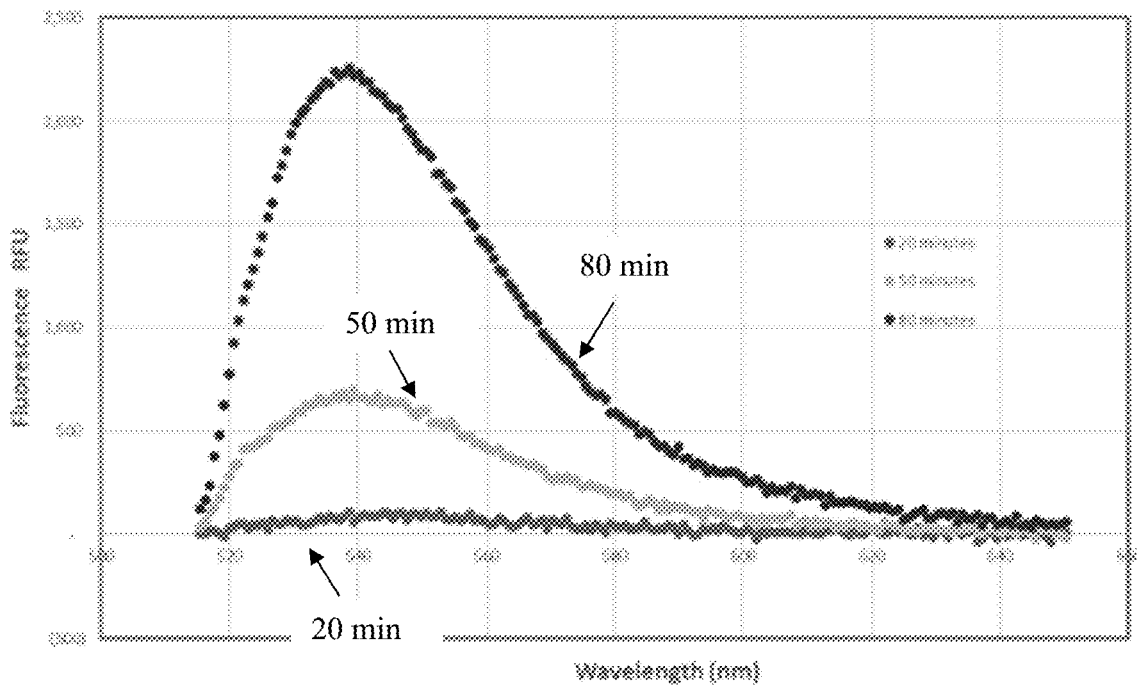
FIG. 14 is a graph schematically illustrating emission of fluorescence by a fluorophore, upon being bound to various concentrations of the target peptide.

Further experimentations show that the methods and the systems described herein are very sensitive and may be used to detect K9K peptide targets in various concentrations, e.g., as low as about 800 femtomolar (fM) (FIGS. 12-14). Generally increasing incubation time will increase fluorescence signals (FIGS. 13-14).

FIG. 12 is a graph schematically illustrating emission of fluorescence by a fluorophore, upon being bound to various concentrations of the target peptide. A series of K9K dilutions (200 pM, 100 pM, 20 pM, 4 pM, and 800 fM) were individually mixed with the fluorophore FlAsH-EDT$_2$ and TCEP. The emitted fluorescence was measured at different time points and demonstrated meaningful increases over the Control.

FIG. 13 is a graph schematically illustrating emission of fluorescence by a fluorophore, upon being bound to the target peptide at various time intervals. K9K peptide (at a final concentration of 800 fM) was treated with the fluorophore FlAsH-EDT$_2$. The emitted fluorescence was measured and graphed, after subtraction of fluorescence of the control, at different time intervals (10, 50, and 80 minutes).

FIG. 14 is a graph schematically illustrating emission of fluorescence by a fluorophore, upon being bound to various concentrations of the target peptide. K9K peptide (at a final concentration of 10 µM) was treated with the fluorophore FlAsH-EDT$_2$. The emitted fluorescence was measured and graphed, after subtraction of fluorescence of the control, at different time intervals (20, 50, and 80 minutes).

Figure 15:
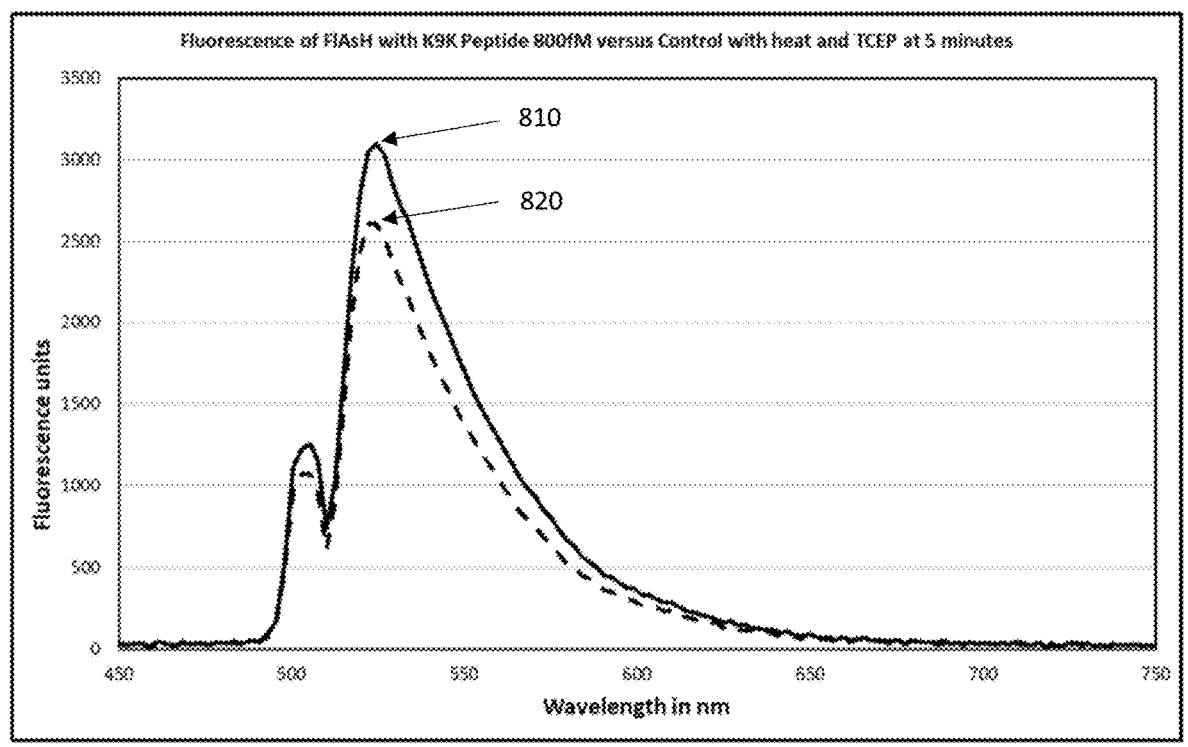
FIG. 15 is a graph schematically illustrating a comparison of spectra from a solution of FlAsH (5 μM) and K9K Peptide (800 femtomolar (fM)), and a FlAsH (5 μM) control solution without K9K Peptide present, when irradiated by a laser generating light at a wavelength of 505 nm.

The FlAsH fluorophore emits higher level of fluorescence when bound to the K9K peptide, compared to the unbound situation. FIG. 15 is a graph schematically illustrating a comparison of spectra from a solution of FlAsH (5 µM) and K9K Peptide (800 femtomolar (fM)), and a FlAsH (5 µM) control solution without K9K Peptide present, when irradiated by laser generating light at a wavelength of 505 nm. Each solution was separately contained in a 7 mL quartz cuvette that comprises a reducing agent (5 mM TCEP). Both cuvettes were placed in a stainless steel measuring cup and heated by a 140° F. (60° C.) coffee mug heater for five minutes. It can be seen that fluorescence from both solutions was maximal at 524 nm and that emission from K9K-FlAsH 810 was meaningfully greater than the emission from FlAsH Control 820. Measurements of fluorescence are made in an exemplary Analyzer described in FIG. 5.

Figure 16:
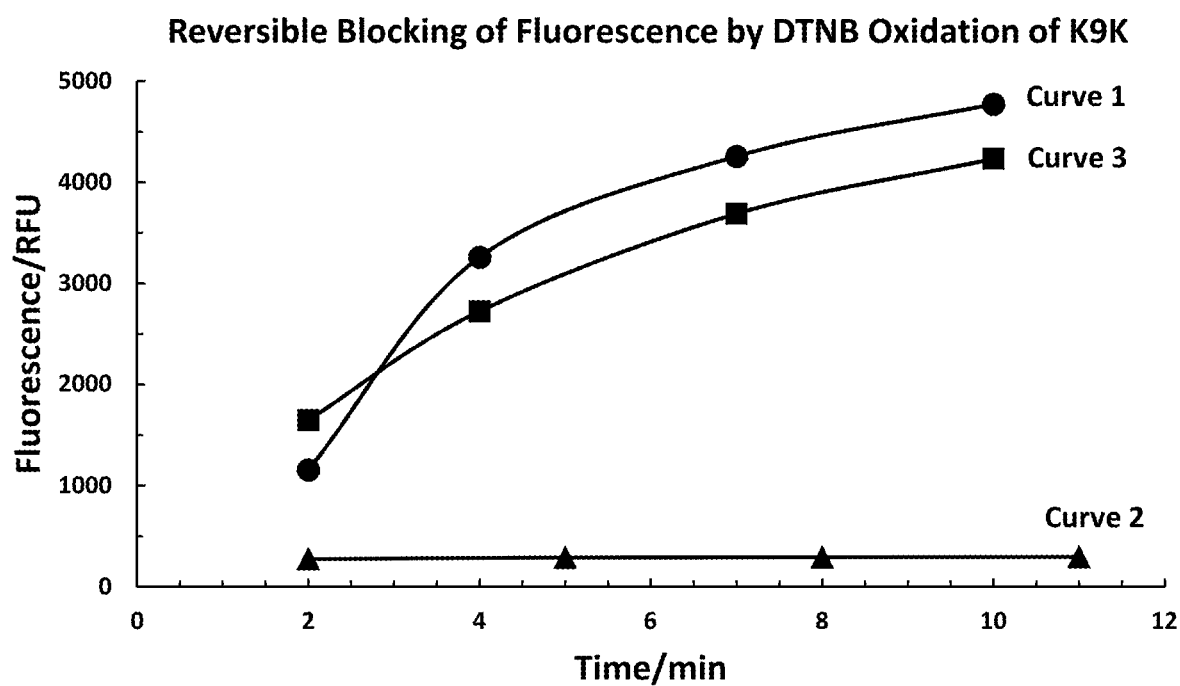
FIG. 16 is a graph schematically illustrating that the FlAsH fluorophore specifically binds to the cysteine sulfhydryl groups of K9K peptide.

The FlAsH fluorophore specifically binds to the cysteine sulfhydryl groups of K9K peptide. FIG. 16 is a graph schematically illustrating that the FlAsH fluorescence may be reversibly blocked by 5,5'-dithiobis(2-nitrobenzoic acid) (DTNB) oxidation of the K9K peptide. An experiment was conducted to determine whether peptide K9K (KGCCSCGSCCK; SEQ ID NO: 3. N terminus to C terminus), whose amino acid sequence matches that of residues 1445-1455 of SARS-CoV-2 spike protein, could be detected with FlAsH. Treatment of peptide K9K with FlAsH was found to rapidly generate intense fluorescence emission (Curve 1). In a separate experiment it was found that prior oxidation of cysteine residues on peptide K9K to disulfides (R—S—S—R) by DTNB, 5,5'-dithiobis(2-nitrobenzoic acid), followed by treatment with FlAsH, prevents generation of fluorescence (Curve 2), which indicates the necessity of cysteine sulfhydryl groups (R—SH) for the generation of FlAsH fluorescence. In another experiment, treatment of oxidized peptide K9K with TCEP, tris(2-carboxyethyl)phosphine, to reduce cysteine disulfides back to cysteine sulfhydryl groups, results in recovery of fluorescence upon treatment with FlAsH (Curve 3). Thus, peptide K9K binds to FlAsH and induces FlAsH to fluoresce: (1) despite the absence of an intervening proline residue between cysteine pairs, which produces a hairpin conformation present in the canonical binding motif of CCPGCC (SEQ ID NO: 4); (2) despite the additional amino acid residues between CC pairs in K9K possibly causing too great of a distance between CC pairs to allow binding of K9K to FlAsH's fixed-distance arsenic atoms; and (3) despite the effect of the constraints imposed by the peptide's primary structure on the need for a conformational change to be induced in FlAsH by the peptide to convert FlAsH from a nonfluorescent conformation to a fluorescent conformation.

Figures 17, 18:
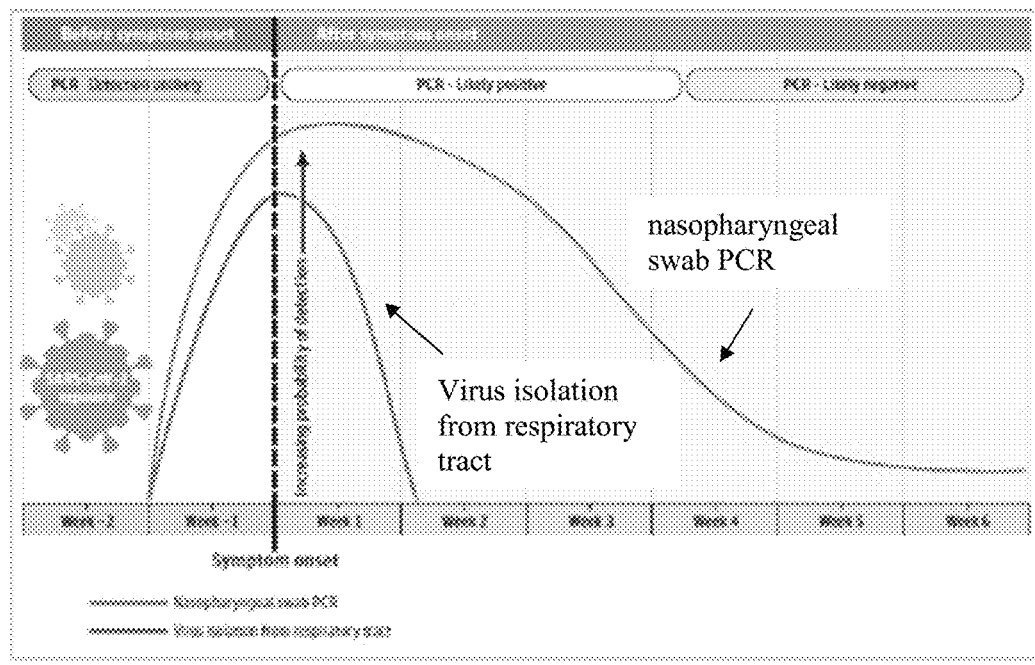
FIG. 17 is a graph schematically illustrating time courses for conventional COVID-19 testing methods, comparing nasopharyngeal swab PCR and virus isolation from respiratory tract.
FIG. 18 is a graph schematically illustrating research data showing risk for symptomatic COVID-19 infection among the 2761 close contacts, showing that contagious period of COVID-19 is the first 5 days of exposure.

The instant disclosure provides a possible quick and reliable detection method for COVID-19 infection (e.g., SARS-CoV-2 in a biological sample from one or more subjects). The 15 second signal reading as described above has a great advantage over traditional detection methods, such as nasopharyngeal swab PCR and isolating virus from the respiratory tract (FIG. 17). FIG. 17 is a graph schematically illustrating time courses for conventional COVID-19 testing methods, comparing nasopharyngeal swab PCR and virus isolation from the respiratory tract.

As the contagious period of COVID-19 is usually during the first 5 days of exposure (FIG. 18), a quick and timely detection method would be very helpful to control the pandemic and to treat patients. FIG. 18 is a graph schematically illustrating research data showing risk for symptomatic COVID-19 infection among the 2761 close contacts, showing that the contagious period of COVID-19 is the first 5 days of exposure. The boxes show that from Day 6 post exposure, the attack rate is zero.

Figure 19:
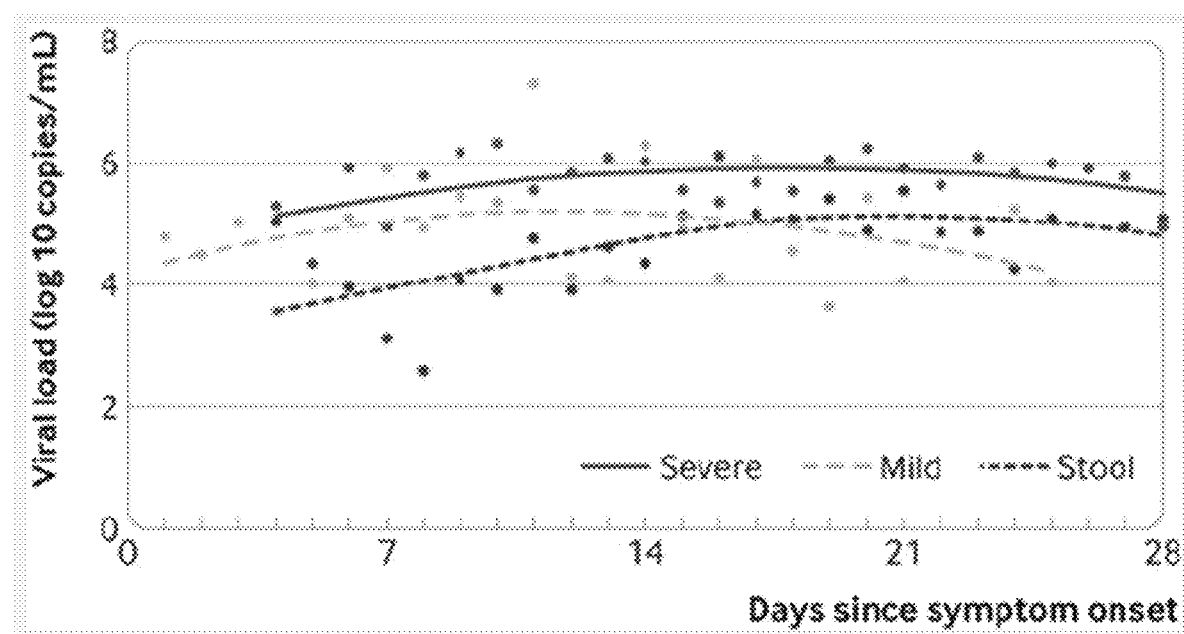
FIG. 19 is a graph comparing viral loads through time since COVID-19 symptom onset.

The abundance of viral load in patients (FIG. 19) also helps the methods and the systems described herein to detect SARS-CoV-2. FIG. 19 is a graph comparing viral loads through time since COVID-19 symptom onset. As shown for severe or mild symptoms, compared to stool samples, viral load is generally about $10^4$ to $10^6$ viruses per milliliter (mL) in respiratory samples.

As shown in Table 2 below, the systems described herein may be provided very cost-effectively, particularly when compared to other testing approaches, which require costly equipment, more time to complete and expensive reagents.

are incorporated by reference. All published foreign patents and patent applications cited herein are hereby incorporated by reference. All other published references, documents, manuscripts and scientific literature cited herein are hereby incorporated by reference. Each of the above is incorporated herein by reference in its entirety for all of its teachings and disclosure, including its methods, apparatuses, reagents, materials, compositions, etc., and can be integrated into the methods, apparatuses, kits and systems described herein.

It will be understood that numerous modifications may be made without departing from the spirit of the invention, and for this reason no limitations which are not expressly set forth in the claims should be assumed or implied. The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. The scope of the disclosure

TABLE 2

Exemplary cost per test at retail pricing
Cost of Supplies per Test of K9K Peptide with TCEP and FlAsH at Retail Pricing

| $ per test | Material | Supplier | Qty | Units | Price | Tax | Ship | Total | Qty per test |
|---|---|---|---|---|---|---|---|---|---|
| 0.098 | Axygen PCR-05-C 0.5 mL Thin Wall Assay Tubes | Lab Genome | 1000 | Item | 87.99 | — | 10.00 | 97.99 | 1 |
| 0.014 | K9K Peptides proxy for spike protein 0.5 mg | Innovagen AB | 0.5 | mg | 40.50 | — | — | 40.50 | 0.000177 |
| 0.199 | TCEP Bond Breaker 0.5M | Thermo Fisher | 5 | ml | 155.00 | 13.56 | 30.00 | 198.56 | 0..005 |
| 0.671 | FlAsH-EDT$_2$ | Cayman Chemical | 1 | mg | 30.00 | 2.48 | 18.00 | 50.48 | 0.013298 |
| $0.98 | | | | | Total Retail Cost of Supplies Per Test of 200 pM K9K | | | | |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

Except as stated immediately above, nothing which has been stated or illustrated is intended or should be interpreted to cause a dedication of any component, step, feature, object, benefit, advantage, or equivalent to the public, regardless of whether it is or is not recited in the claims.

What is claimed is:

1. A method of detecting SARS-CoV-2 in a biological sample, comprising:

i) providing a composition for detection, comprising the biological sample and a fluorophore, wherein the fluorophore is capable of binding chemically with KGCCSCGSCCK (SEQ ID NO:3) within SARS-CoV-2 spike protein;

ii) providing to the composition for detection a light comprising a first wavelength range that is maximal at wavelength $\lambda_1$ capable of energizing the fluorophore after binding chemically with SEQ ID NO:3 within SARS-CoV-2 spike protein;

iii) measuring fluorescence emitted by the fluorophore at a second wavelength range that is maximal at wavelength $\lambda_2$, wherein SARS-CoV-2 is detected in the biological sample if the level of the detected fluorescence in iii) is higher than a control sample fluorescence level; and iv) measuring fluorescence emitted by a second fluorophore at a third wavelength range that is maximal at wavelength $\lambda_3$;

wherein the fluorophore comprises the structure of:

(a) Formula I:

Formula I wherein,
W is a hydrogen (H) or bromine (Br);
X is a hydrogen (H) or bromine (Br);
Y is an oxygen (O) or sulfur (S); and
Z is a nitrogen (N) or C—$C_6H_4COOH$,
　or a chemically acceptable salt or precursor thereof;

(b) Formula II:

Formula II ($FlAsH-EDT_2$)

or a chemically acceptable salt or precursor thereof; or (c) Formula III:

*Formula III*

(ReAsH-EDT$_2$)

or a chemically acceptable salt or precursor thereof.

2. The method of claim 1, wherein the fluorophore comprises the structure of Formula I:

*Formula I* wherein,
W is a hydrogen (H) or bromine (Br);
X is a hydrogen (H) or bromine (Br);
Y is an oxygen (O) or sulfur (S); and
Z is a nitrogen (N) or C—C$_6$H$_4$COOH,
or a chemically acceptable salt or precursor thereof.

3. The method of claim 1, wherein the fluorophore comprises the structure of Formula II or III:

*Formula II*

(FlAsH-EDT$_2$)

or

*Formula III*

(ReAsH-EDT$_2$)

or a chemically acceptable salt or precursor thereof.

4. The method of claim 1, wherein $\lambda_i$ is at about 508 nm or about 593 nm.

5. The method of claim 1, wherein the fluorophore is capable of:
   i) binding chemically with a tetracysteine sequence of SEQ ID NO:3 within SARS-CoV-2 spike protein and/or cysteine pairs in adjacent proteins; and/or
   ii) binding chemically with a tetracysteine sequence of SEQ ID NO:3 within SARS-CoV-2 spike protein and/or cysteine pairs in adjacent spike proteins.

6. The method of claim 1, wherein the biological sample
   i) is derived from saliva, oral fluid, nasal drainage fluid, nasal swab residue, nasopharyngeal swab residue, pharyngeal swab residue, upper and/or lower respiratory tract aspirate, or stool of one or more subjects; and/or
   ii) comprises one or more body fluids from one or more subjects.

7. The method of claim 1, wherein the composition for detection further comprises a reducing agent selected from the group consisting of tris(2-carboxyethyl)phosphine (TCEP), British anti-Lewisite (BAL, a.k.a., dimercaprol), 2-aminoethanethiol (cysteamine), cysteine, dithiobutylamine (DTBA), dithioerythritol (DTE), dithiothreitol (DTT), glutathione, β-mercaptoethanol (β-ME), sodium 2-mercaptoethanesulfonate (MESNa), or their chemically acceptable salts.

8. The method of claim 1, further comprising:
   i) heating the composition for detection to at least a temperature $T_1$, prior to the measuring in step iii) or iv);
   ii) spinning the biological sample in a centrifuge to concentrate any SARS-CoV-2 in the biological sample, prior to addition of the fluorophore; and/or
   iii) adhering any SARS-CoV-2 in the biological sample with a viral selective surface or membrane, prior to addition of the fluorophore or the second fluorophore, or with an immobilized fluorophore.

9. The method of claim 1, wherein the light in step ii) passes through the composition for detection a plurality of times
   i) to enhance light absorption while measuring in step iii) or iv); and/or
   ii) by reflection from a mirror and/or other reflecting surfaces.

10. A composition comprising a biological sample comprising SARS-CoV-2 and a fluorophore, wherein the fluorophore is capable of binding chemically with SEQ ID NO:3 within SARS-CoV-2 spike protein, and wherein the fluorophore, when bound to SARS-CoV-2, is capable of: 1) being energized by a light comprising a first wavelength range that is maximal at wavelength $\lambda_1$; and 2) emitting fluorescence at a second wavelength range that is maximal at wavelength $\lambda_2$;
wherein the fluorophore comprises the structure of:
   (a) Formula I:

*Formula I* wherein,
W is a hydrogen (H) or bromine (Br);
X is a hydrogen (H) or bromine (Br);
Y is an oxygen (O) or sulfur (S); and
Z is a nitrogen (N) or C—C$_6$H$_4$COOH,
or a chemically acceptable salt or precursor thereof;
(b) Formula II:

Formula II (FlAsH-EDT$_2$)

or a chemically acceptable salt or precursor thereof; or
(c) Formula III:

Formula III (ReAsH-EDT$_2$)

or a chemically acceptable salt or precursor thereof.

11. The composition of claim 10, wherein the fluorophore comprises the structure of Formula I:

wherein,
W is a hydrogen (H) or bromine (Br);
X is a hydrogen (H) or bromine (Br);
Y is an oxygen (O) or sulfur (S); and
Z is a nitrogen (N) or C—C$_6$H$_4$COOH,
or a chemically acceptable salt or precursor thereof.

12. The composition of claim 10, wherein the fluorophore comprises the structure of Formula II or III:

Formula II (FlAsH-EDT$_2$)

Formula III (ReAsH-EDT$_2$)

or a chemically acceptable salt or precursor thereof.

13. The composition of claim 10, wherein $\lambda_1$ is at about 508 nm or about 593 nm.

14. The composition of claim 10, wherein the fluorophore is capable of:
   i) binding chemically with a tetracysteine sequence of a SARS-CoV-2 protein, and/or cysteine pairs in adjacent proteins, and/or a cysteine pair with two separated cysteine residues within a single protein or adjacent proteins; and/or
   ii) binding chemically with a tetracysteine sequence of SEQ ID NO:3 within SARS-CoV-2 spike protein and/or cysteine pairs in adjacent spike proteins.

15. The composition of claim 10, wherein the biological sample
   i) is derived from saliva, oral fluid, nasal drainage fluid, nasal swab residue, nasopharyngeal swab residue, pharyngeal swab residue, upper and/or lower respiratory tract aspirate, or stool of one or more subjects;
   ii) comprises a body fluid of one or more subjects; and/or
   iii) is filtered to remove debris, cells, and/or tissues from the one or more subjects, prior to addition of the fluorophore.

16. The composition of claim 10, further comprising a reducing agent selected from the group consisting of tris(2-carboxyethyl)phosphine (TCEP), British anti-Lewisite (BAL, a.k.a., dimercaprol), 2-aminoethanethiol (cysteamine), cysteine, dithiobutylamine (DTBA), dithioerythritol (DTE), dithiothreitol (DTT), glutathione, β-mercaptoethanol (β-ME), sodium 2-mercaptoethanesulfonate (MESNa), or their chemically acceptable salts.

17. A kit for detection of the existence of SARS-CoV-2 in a biological sample comprising:
   i) a composition of claim 10; and
   ii) optionally, a manual of instructions.

18. The kit of claim 17, further comprising
i) a device to stimulate production of the biological sample by one or more subjects; and/or
ii) a viral selective surface or membrane, or an adhered fluorophore, capable of adhering any SARS-CoV-2 in the biological sample.

19. A system for detection of the existence of SARS-CoV-2 in a biological sample, comprising:
i) a first device capable of collecting or containing a biological sample;
ii) a second device containing a composition of claim 10;
iii) an emitter capable of emitting light comprising the first wavelength range, that is maximal at wavelength $\lambda_1$ through the composition in ii) when mixed with the biological sample; and
iv) a detector capable of measuring fluorescence emitted by the fluorophore at the second wavelength range, that is maximal at wavelength $\lambda_2$ or the second fluorophore at the third wavelength range, that is maximal at wavelength $\lambda_3$).

20. The method of claim 1 wherein the fluorophore is capable of binding chemically with CCSCGSCC (SEQ ID NO: 2) within SARS-CoV-2 spike protein.

21. The composition of claim 10, wherein the fluorophore is capable of binding chemically with CCSCGSCC (SEQ ID NO: 2) within SARS-CoV-2 spike protein.

* * * * *

UNITED STATES PATENT AND TRADEMARK OFFICE
CERTIFICATE OF CORRECTION

PATENT NO. : 11,320,434 B2
APPLICATION NO. : 17/338640
DATED : May 3, 2022
INVENTOR(S) : Rose et al.

Page 1 of 1

It is certified that error appears in the above-identified patent and that said Letters Patent is hereby corrected as shown below:

In the Claims

Column 34, Claim 4, Lines 1 and 2, replace "The method of claim 1, wherein Xi is at about 508 nm or about 593 nm." with -- The method of claim 1, wherein $\lambda 1$ is at about 508 nm or about 593 nm. --.

Signed and Sealed this
Fifth Day of July, 2022

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 33
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Cysteine residues
<220> FEATURE:
<221> NAME/KEY: MISC_FEATURE
<222> LOCATION: (3)..(31)
<223> OTHER INFORMATION: Bases 3-31 may be present or absent
<220> FEATURE:
<221> NAME/KEY: MISC_FEATURE
<222> LOCATION: (32)..(33)
<223> OTHER INFORMATION: Cysteine residues

<400> SEQUENCE: 1

Cys Cys Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Cys
            20                  25                  30

Cys
```

```
<210> SEQ ID NO 2
<211> LENGTH: 8
<212> TYPE: PRT
<213> ORGANISM: Artificial sequence
<220> FEATURE:
<223> OTHER INFORMATION: Synthetic construct

<400> SEQUENCE: 2

Cys Cys Ser Cys Gly Ser Cys Cys
1               5

<210> SEQ ID NO 3
<211> LENGTH: 11
<212> TYPE: PRT
<213> ORGANISM: Artificial sequence
<220> FEATURE:
<223> OTHER INFORMATION: Synthetic construct

<400> SEQUENCE: 3

Lys Gly Cys Cys Ser Cys Gly Ser Cys Cys Lys
1               5                   10

<210> SEQ ID NO 4
<211> LENGTH: 6
<212> TYPE: PRT
<213> ORGANISM: Artificial sequence
<220> FEATURE:
<223> OTHER INFORMATION: Synthetic construct

<400> SEQUENCE: 4

Cys Cys Pro Gly Cys Cys
1               5
```